(12) United States Patent
Villaumie

(10) Patent No.: US 8,130,376 B2
(45) Date of Patent: Mar. 6, 2012

(54) OPTICAL DEVICES, SPECTROSCOPIC SYSTEMS AND METHODS FOR DETECTING SCATTERED LIGHT

(75) Inventor: Julien S. Villaumie, Clonmel (IE)

(73) Assignee: Avalon Instruments Ltd., Belfast (IE)

( * ) Notice: Subject to any disclaimer, the term of this patent is extended or adjusted under 35 U.S.C. 154(b) by 177 days.

(21) Appl. No.: 12/478,381

(22) Filed: Jun. 4, 2009

(65) Prior Publication Data
US 2010/0110423 A1    May 6, 2010

Related U.S. Application Data

(60) Provisional application No. 61/059,131, filed on Jun. 5, 2008.

(51) Int. Cl.
*G01J 3/44*    (2006.01)
*G01N 21/65*    (2006.01)

(52) U.S. Cl. ........................................ 356/301; 359/589
(58) Field of Classification Search .............. 359/633, 359/634, 636, 578, 579, 590; 356/454, 519, 356/301
See application file for complete search history.

(56) References Cited

U.S. PATENT DOCUMENTS

| | | | |
|---|---|---|---|
| 6,064,897 A | 5/2000 | Lindberg et al. | |
| 2001/0055113 A1 | 12/2001 | Yin | |
| 2003/0099009 A1* | 5/2003 | Noda et al. | 359/15 |
| 2005/0124870 A1 | 6/2005 | Lipson | |
| 2007/0019191 A1 | 1/2007 | Marrow | |
| 2007/0205379 A1 | 9/2007 | Nelson et al. | |
| 2008/0123104 A1* | 5/2008 | Miron | 356/519 |

* cited by examiner

*Primary Examiner* — F. L. Evans
(74) *Attorney, Agent, or Firm* — Lando & Anastasi, LLP

(57) ABSTRACT

Certain examples described herein are directed to optical devices and systems that include first and second optical elements. In some examples, the first optical element may be configured to pass light received from an excitation source, and the second optical element may be optically coupled to the first optical element and may be configured to reflect incident light from the first optical element back to the first optical element and configured to pass the light reflected from the first optical element. Methods using the devices and systems are also described.

20 Claims, 16 Drawing Sheets

OPTICAL DEVICES, SPECTROSCOPIC SYSTEMS AND METHODS FOR DETECTING SCATTERED LIGHT

PRIORITY APPLICATION

This application claims priority to U.S. Provisional Application No. 61/059,131 filed on Jun. 5, 2008, the entire disclosure of which is hereby incorporated herein by reference for all purposes.

TECHNOLOGICAL FIELD

Certain embodiments disclosed herein relate generally to optical devices. More particularly, certain embodiments disclosed herein relate to optical devices and optical configurations for use in multiplexed systems, such as those configured to detect multiple emitted or scattered wavelengths.

BACKGROUND

When light passes through a transparent medium, the light may be scattered in all directions. Two common light scattering phenomena are Rayleigh scattering and Raman scattering. In Rayleigh scattering, the light is scattered by molecules whose dimensions are smaller than the wavelength of radiation. The blueness of the sky, which results from the increased scattering of shorter wavelengths of the visible spectrum, is an example of Rayleigh scattering.

In Raman scattering, the wavelength of the scattered light is shifted from the wavelength of the incident light. The exact shifts in wavelength depend on the chemical structure of the medium or sample scattering the light. Raman lines having wavelengths higher than the incident wavelength are referred to as Stokes lines and those having wavelengths lower than the incident wavelengths are referred to as anti-Stokes lines. The intensities of Raman lines can be 0.001% or less when compared to the intensity of the incident light. Thus, detection of Raman scattering remains difficult.

SUMMARY

In one aspect, an optical device comprising first and second optical elements is disclosed. In certain examples, the first optical element may be angle-tuned to pass light received from an excitation source, and the second optical element may be optically coupled to the first optical element and may be angle-tuned to reflect incident light from the first optical element back to the first optical element and configured to pass light reflected from the first optical element.

In certain embodiments, the optical device may further comprise a collection device. In some examples, the collection device may be configured to receive sample light incident on the first and second optical elements and passed by the first and second optical elements to the collection device. In certain examples, the first and second optical element may each be long pass filters. In some embodiments, the optical device may further comprise a detector optically coupled to the collection device. In certain examples, the long pass filters may be further configured to pass scattered or emitted light from a sample to a detector optically coupled to the sample. In other examples, the collection device may comprise an optical fiber bundle. In additional examples, the detector may be a charge-coupled device. In certain embodiments, the optical device may be configured to detect Raman scattered light. In yet other examples, the optical device may further comprise at least one additional optical element.

In another aspect, a spectroscopic system comprising an excitation source, first and second optical elements, a sample space, and a collection device is provided. In certain embodiments, the excitation source may be configured to provide light. In some examples, the first optical element may be optically coupled to the excitation source and configured to pass light received from the excitation source. In other examples, the second optical element may be optically coupled to the first optical element, and the first and second optical elements may each be angle-tuned such that the second optical element is configured to reflect incident light from the first optical element back to the first optical element and to pass light reflected from the first optical element. In some examples, the sample space may be optically coupled to the second optical element and configured to receive the light passed by the second optical element. In certain examples, the collection device may be optically coupled to the second optical element, in which the first and second optical elements are further configured to receive emitted light, e.g., scattered light, from a sample in the sample space and to pass the emitted light of the scattered light to the collection device.

In certain embodiments, the excitation source may comprise a plurality of optical fibers each configured to provide light to the first optical element. In other examples, the collection device may comprise a plurality of optical fibers each configured to receive a light emission from a different sample in a multi-sample device in the sample space. In additional examples, the system may comprise at least one additional optical element. In yet other examples, the system may further comprise a detector optically coupled to the collection device such as, for example, a detector optical coupled to plurality of optical fibers each configured to receive a light emission. In some examples, the system may be configured to detect light emissions or Raman scattered light.

In an additional aspect, a system comprising means for providing light to a sample space, a first optical path between the means for providing light and the sample space, and first and second optical means in the first optical path, the first optical means for passing light received from the means for providing light, and the second optical means optically coupled to the first optical means, the second optical means for reflecting incident light from the first optical means back to the first optical means and for passing the light reflected from the first optical means to the sample space is disclosed.

In certain embodiments, the system may further comprise means for detecting light emitted from the sample space, wherein said means for detecting light is optically coupled to the sample space through a second optical path and wherein the first optical means and the second optical means are in the second optical path and pass emitted or scattered light from the sample space to the means for detecting along the second optical path. In other examples, the first optical means and said second optical means may each be a long pass filter. In yet other examples, the means for providing light comprise an optical fiber bundle optically coupled to a laser. In certain examples, the means for detecting light may comprise an optical fiber bundle optically coupled to a charge-coupled device.

In another aspect, a method comprising selecting a first angle for a first optical element, selecting a second angle for a second optical element that is optically coupled to the first optical element, and angle tuning the first and second optical elements by adjusting the selected first and second angles such that the first optical element is configured to pass light received from an excitation source, and the second optical element is configured to reflect incident light from the first optical element back to the first optical element and configured to pass the light reflected from the first optical element.

In an additional aspect, a method of detecting emitted or scattered light comprising configuring a system with at least a first and second long pass filter, angle-tuning the first and second long pass filters such that the first long pass filter is configured to pass light received from an excitation source, and the second long pass filter is configured to reflect incident light from the first long pass filter back to the first long pass filter and configured to pass the light reflected from the first long pass filter to a sample, and detecting emitted light from the sample with a detector is disclosed.

Additional aspects, examples, embodiments and features are described in more detail below.

BRIEF DESCRIPTION OF THE FIGURES

Certain examples are described below with reference to the accompanying figures in which.

The angles, dimensions and exact sizes of the components shown in the figures are not necessarily drawn to scale. In particular, the exact angle of one component, relative to another component, may vary as described further below. The sizes and dimensions of the components in the figures, relative to the sizes and dimensions of other components in the figures, are shown merely for illustration and should not be construed as limiting the scope of the technology.

DETAILED DESCRIPTION

Certain illustrative embodiments are described below to illustrate some of the uses, advantages and features of the technology described herein. Embodiments of the optical devices and configurations described herein may be used, for example, in or as multiplexing systems configured to measure light emission simultaneously from a plurality of samples, to measure light emission simultaneously from a plurality of locations within a single sample, and/or to measure a plurality of light emissions simultaneously within a single sample and from a plurality of different samples. Other uses are also possible using the devices, systems and methods disclosed herein. Certain embodiments described are particularly suited for use with multi-well plates such as, for example, 96-well plates, 384-well plates or larger multi-well plates. In addition, the devices may be used to measure light emission from fluorescence or phosphorescence emission, Raman scattering or other suitable light emission and/or scattering processes. The term "emitted light" is used herein to refer to light emission, scattered light and other processes where a sample provides light after excitation by a light or energy source.

Figure 1:
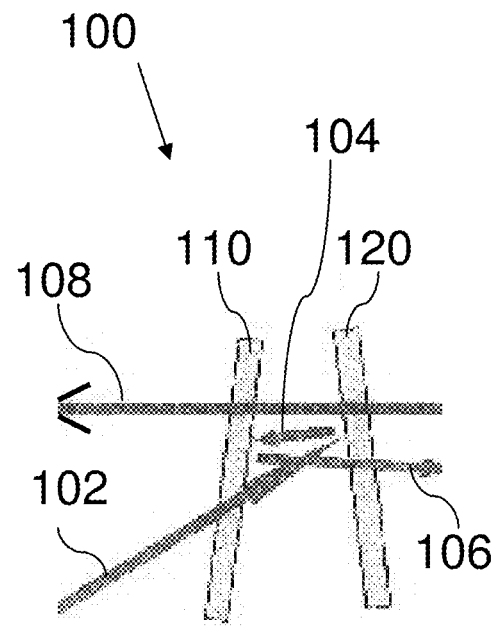
FIG. 1 is a schematic of two optical elements, in accordance with certain examples.

In certain examples, an optical device comprising first and second optical elements is provided. Referring to FIG. 1, an optical device 100 comprises a first optical element 110 and a second optical element 120 optically coupled to the first optical element 110. In certain examples, the first and second optical elements 110 and 120, respectively, may each be a long pass filter that is selected to pass light from an excitation source such as, for example, a laser. The long pass filters may be selected to match the wavelength of the excitation source. For example, where a 532 nm laser is used, each of the first and second optical elements may be a 532 nm long pass filter. Where a 785 nm laser is used, each of the first and second optical elements may be a 785 nm long pass filter. The long pass filter passes light with longer wavelengths and filters or blocks light, for example, by reflecting it, with shorter wavelengths. For example, a 532 nm long pass filter blocks substantially all light at and below 532 nm and passes light above 532 nm. In certain examples, each of the first and second optical elements may be a long pass filter and at least one additional optical element such as, for example, a lens, grating, long pass filter, short pass filter or the like may also be used with the first and second optical elements.

In certain instances herein, the first and second optical elements 110 and 120, respectively, can be angle-tuned such that light 102 from, for example, a light source, is passed by the first optical element 110. The angle between the light source and the first optical element 110 may be selected such that both polarizations of light from the light source (s polarization—components perpendicular to the plane of the page and p polarization—components parallel to the plane of the page) are passed by the first optical element 110. The passed light 102 is then incident on the second optical element 120. The angle of the second optical element 120, with respect to the first optical element 110, may be selected such that the second optical element 120 reflects substantially all of the light back to the first optical element 110. When the reflected light 104 is incident on the first optical element 110, the angles of incidence may be selected such that the first optical element 110 does not pass the reflected light 104 but instead blocks the reflected light 104 and reflects it back to the second optical element 120 as reflected light 106. The reflected light 106 then reaches the second optical element 120, and the selected angles of incidence permit passage of all the reflected light 106 to a sample (not shown) by the second optical element 120. Such angle tuning provide numerous advantages including, for example, filtering out resonance lines from the excitation source (and/or Raman light generated by the fiber optic carrying the excitation light) that have wavelengths shorter and/or longer than the desired excitation wavelength. By filtering out the resonance lines, the overall precision and accuracy of detecting emitted or scattered light from a sample may be improved.

In certain embodiments, the reflected light 106 may be provided to one or more samples and used to excite the one or more samples such that the sample emits or scatters light for example, by fluorescence, phosphorescence or Raman scattering. Fluorescence refers to light emission occurring during decay from an excited singlet state to a ground singlet state. Phosphorescence refers to light emission occurring during decay from an excited triplet state to a ground singlet state. Raman scattering refers to scattering of photons that are shifted in frequency (inelastic scattering). The first and second optical elements 110 and 120 may receive the emitted or scattered light 108 and be configured to pass the emitted or scattered light 108 to a collection device and/or a detector.

Figure 2:
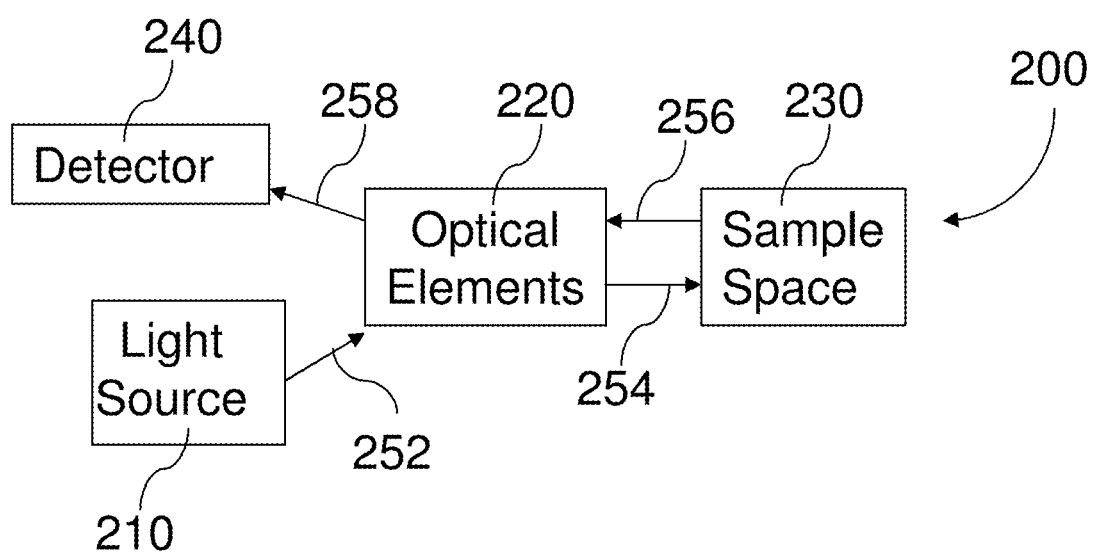
FIG. 2 is a diagram of an optical system, in accordance with certain examples.

An illustrative system, in accordance with certain embodiments, is shown in the diagram of FIG. 2. The system 200 comprises a light source 210, optical elements 220, a sample space 230 and a detector 240. In operation, light 252 from the light source 210 is provided to the optical elements 220. The light may be tuned by the optical elements 220 as described, for example, in reference to FIG. 1. Light 254 is passed by the optical elements 220 to the sample space 230. Emitted light 256, e.g., scattered light, from a sample in the sample space 230 may be provided back to the optical elements 220 and onto a detector 240, as light 258, for detection. In some examples, a single sample may emit light for detection, whereas in other examples described herein, a plurality of samples may simultaneously emit light and each of the light emissions may be simultaneously detected by the detector 240.

In certain examples, the light source 210 may be, or may include, a deuterium lamp, an arc lamp, a vapor lamp, a cathode lamp, an electrodeless discharge lamp, a laser, a light emitting diode, or other suitable light emitting devices. In embodiments where the light source emits multiple different wavelengths, it may be desirable to select a single wavelength or a small range of wavelengths from the light source. Such selection may be accomplished using suitable methods and devices such as, for example, filters, gratings, monochromators and the like. In some examples, the light source may be optically coupled to a plurality of fiber optical bundles such that two or more discrete light beams or spots may be incident on the optical elements. By providing discrete light beams or spots to a sample, selected areas, such as two or more wells in a multi-well plate, may be illuminated.

In some examples, the optical elements 220 may include at least one long pass filter and more particularly, at least two long pass filters that are angle tuned. In some examples, the optical elements 220 includes a first and second long pass filter and at least one additional optical element such as, for example, a lens, grating, prism, short pass filter, long pass filter or other suitable optical devices. As discussed further below, in embodiments where first and second long pass filters are used, the long pass filters may be angle tuned such that a desired wavelength of light from the excitation source and/or the sample is passed and other non-desirable wavelengths of light are rejected. In some embodiments, the optical elements may be packaged such that they can be dropped into an existing instrument and provide the proper alignment and/or angles for performing optical measurements. Such packaging may include, for example, positioning of the optical elements within an optically transparent housing so that the end user is not required to align the various elements.

In certain embodiments, the sample space 230 may include a sample holder configured to retain a sample device of a desired dimension and/or shape. In examples where the sample space is configured to receive a 96-well, 384-well or other multi-well plate, the sample holder may comprise a generally flat surface that is configured to receive the plate. The surface may be non-reflective such that light emitted or scattered toward the surface is absorbed rather than being reflected. In embodiments where the multi-well plate comprises a non-reflective coating on its inner surfaces, the sample surface need not be anti-reflective. In some examples, the sample space 230 may include temperature control such that the desired reaction or study in the wells of the plate may be maintained at a controlled temperature. In other examples, the sample space 230 may include a moveable stage such that the exact position of the sample holder can be tuned or adjusted or so that the plate can be agitated for mixing or the like. Additional suitable features for including in the sample space will be readily selected by the person of ordinary skill in the art, given the benefit of this disclosure.

In certain embodiments, the detector 240 may be configured to receive light emitted or scattered from a sample. The scattered or emitted light may be passed by the optical elements to the detector. In some examples, the scattered or emitted light may be focused using one or more lenses prior to passage to the detector. In other examples, a filter or grating may be placed between the optical elements and the detector such that a wavelength or wavelength range of light is passed to the detector. In certain examples, the detector may include such filters or lenses. In some examples, the detector may be configured to receive discrete spots or beams of light from the sample. In such instances, the detector may be optically coupled to a plurality of optical fibers such that each beam or spot from the sample may be incident on its own respective optical fiber. The beams may be individually detected or may be simultaneously detected depending on the exact type of detector used. In some examples, the detector may include one or more of a photomultiplier tube, a charge-coupled device, a diode or a diode array. The detector may also include apertures or slits whose width can be tuned or selected to permit a desired amount of light to enter the detector. The detector may further include temperature control, one or more communication devices to provide data to a system or the like.

In accordance with certain examples, the systems described herein may be controlled or used with, at least in part, a computer system. The computer systems may be, for example, general-purpose computers such as those based on Unix, Intel PENTIUM-type processor, Motorola PowerPC, Sun UltraSPARC, Hewlett-Packard PA-RISC processors, or any other type of processor. It should be appreciated that one or more of any type computer system may be used according to various embodiments of the technology. Further, the system may be located on a single computer or may be distributed among a plurality of computers attached by a communications network. A general-purpose computer system according to one embodiment may be configured to perform any of the described functions including but not limited to: data acquisition, data analysis, angle tuning of the optical elements by, for example, actuating a motor coupled to a moveable stage where the optical elements are mounted or fixed and the like. It should be appreciated that the system may perform other functions, including network communication, and the technology is not limited to having any particular function or set of functions.

For example, various aspects may be implemented as specialized software executing in a general-purpose computer system. The computer system may include a processor connected to one or more memory devices, such as a disk drive, memory, or other device for storing data. The memory is typically used for storing programs and data during operation of the computer system. Components of computer system may be coupled by an interconnection mechanism, which may include one or more busses (e.g., between components that are integrated within a same machine) and/or a network (e.g., between components that reside on separate discrete machines). The interconnection mechanism enables communications (e.g., data, instructions) to be exchanged between system components. The computer system typically is electrically coupled to an interface on the system such that electrical signals may be provided from the system to the computer system for storage and/or processing.

The computer system may also include one or more input devices, for example, a keyboard, mouse, trackball, microphone, touch screen, and one or more output devices, for example, a printing device, status or other LEDs, display screen, speaker. In addition, the computer system may contain one or more interfaces that connect computer system to a communication network (in addition or as an alternative to the interconnection mechanism). The storage system of the computer typically includes a computer readable and writeable nonvolatile recording medium in which signals are stored that define a program to be executed by the processor or information stored on or in the medium to be processed by the program. For example, the angles used to tune the optical elements may be stored on the medium. The medium may, for example, be a disk or flash memory. Typically, in operation, the processor causes data to be read from the nonvolatile recording medium into another memory that allows for faster access to the information by the processor than does the medium. This memory is typically a volatile, random access memory such as a dynamic random access memory (DRAM) or static memory (SRAM). It may be located in storage system, as shown, or in memory system. The processor generally manipulates the data within the integrated circuit memory and then copies the data to the medium after processing is completed. A variety of mechanisms are known for managing data movement between the medium and the integrated circuit memory element, and the technology is not limited thereto. The technology is not limited to a particular memory system or storage system.

The computer system may also include specially-programmed, special-purpose hardware, for example, an application-specific integrated circuit (ASIC). Aspects of the technology may be implemented in software, hardware or firmware, or any combination thereof. Further, such methods, acts, systems, system elements and components thereof may be implemented as part of the computer system described above or as an independent component.

In some examples, the computer system may be a general-purpose computer system that is programmable using a high-level computer programming language. The computer system may be also implemented using specially programmed, special purpose hardware. In the computer system, the processor is typically a commercially available processor such as the well-known Pentium class processor available from the Intel Corporation. Many other processors are available. Such a processor usually executes an operating system which may be, for example, the Windows 95, Windows 98, Windows NT, Windows 2000 (Windows ME), Windows XP or Windows Vista operating systems available from the Microsoft Corporation, MAC OS System X operating system available from Apple Computer, the Solaris operating system available from Sun Microsystems, or UNIX or Linux operating systems available from various sources. Many other operating systems may be used. In addition or alternative to a processor, the computer system may include a controller such as for example and 8-bit or 16-bit controller. Other controllers such as 32-bit or higher controller may also be used in place of a processor or in addition to the processor of the computer system.

The processor and operating system together define a computer platform for which application programs in high-level programming languages can be written. It should be understood that the technology is not limited to a particular computer system platform, processor, operating system, or network. Also, it should be apparent to those skilled in the art that the present technology is not limited to a specific programming language or computer system. Further, it should be appreciated that other appropriate programming languages and other appropriate computer systems could also be used.

In certain examples, the hardware or software is configured to implement cognitive architecture, neural networks or other suitable implementations. For example, desired angles of incidence for the components of the system may be stored in the system and used where a desired assay or measurement is to be performed. Such a configuration permits recall of known parameters for use in successive measurements, which can simplify the functionality and increase the overall ease of use by an end user.

One or more portions of the computer system may be distributed across one or more computer systems coupled to a communications network. These computer systems also may be general-purpose computer systems. For example, various aspects may be distributed among one or more computer systems configured to provide a service (e.g., servers) to one or more client computers, or to perform an overall task as part of a distributed system. For example, various aspects may be performed on a client-server or multi-tier system that includes components distributed among one or more server systems that perform various functions according to various embodiments. These components may be executable, intermediate (e.g., IL) or interpreted (e.g., Java) code which communicate over a communication network (e.g., the Internet) using a communication protocol (e.g., TCP/IP). It should also be appreciated that the technology is not limited to executing on any particular system or group of systems. Also, it should be appreciated that the technology is not limited to any particular distributed architecture, network, or communication protocol.

Various embodiments may be programmed using an object-oriented programming language, such as SmallTalk, Basic, Java, C++, Ada, or C# (C-Sharp). Other object-oriented programming languages may also be used. Alternatively, functional, scripting, and/or logical programming languages may be used. Various aspects may be implemented in a non-programmed environment (e.g., documents created in HTML, XML or other format that, when viewed in a window of a browser program, render aspects of a graphical-user interface (GUI) or perform other functions). Various aspects may be implemented as programmed or non-programmed elements, or any combination thereof.

In certain examples, a user interface may be provided such that a user may enter desired parameters such as, for example, the number of wells in the multi-well plate, sample holder temperatures, acquisition rates and times and the like. Other features for inclusion in a user interface will be readily selected by the person of ordinary skill in the art, given the benefit of this disclosure.

In accordance with certain examples, the devices and systems disclosed herein may be used to detect light emission and/or scattering from many different types of assays. Illustrative assays include, but are not limited to, solid phase assays, chemical reactions, binding assays, hybridization assays, enzymatic assays, clinical diagnostic assays, immunoassays such as ELISA assays, polymerization processes and other suitable assays or processes that may be monitored using emitted or scattered light.

In some examples, the systems disclosed herein may include additional components such as, for example, an autoloader. The autoloader may be configured to load samples sequentially into and out of the system such that the system may perform measurements without user intervention or monitoring. The autoloader may comprise, for example, a robotic arm and/or motor that can securely grip the samples and load them into a desired position in the system. The system may include other electrical components such as operational amplifiers, gain control devices and the like. The system may include a bar code reader so that each sample may be encoded with a bar code and the measurements of each sample can be associated with its respective bar code. In some examples, each well of a multi-well plate may include an identification device, such as a bar code or chip, so that each sample has its own individual address within a plate. Additional components and features for including in the devices and systems disclosed herein will be readily selected by the person of ordinary skill in the art, given the benefit of this disclosure.

In certain embodiments of the devices and systems described herein, the angle between the optical elements 110 and 120 may be selected such that a desired amount and/or wavelength of the light is passed. Such angle selection is referred to in certain instances as "angle tuning." For example, it may be desirable to pass both polarizations of the light from the excitation source. If the normal incidence of the first optical element passes 99% of the light at a wavelength $\lambda_{99\% T}$, then to determine the minimum angle the following equation may be used $$\theta_{99\% T, \lambda laser} = \sin^{-1}\left(n_{eff}\sqrt{1 - \left(\frac{\lambda_{laser}}{\lambda_{99\% T, 0°}}\right)^2}\right)$$

where $n_{eff}$ varies with the particular element used and is provided by the manufacturer. For certain examples described below, $n_{eff}$ represents 2.08 for the s-polarization, 1.62 for the p-polarization, $\lambda_{laser}$ is the wavelength of the excitation source and $\theta_{99\% T, \lambda laser}$ is the angle. The angle should be larger for the s-polarization than the p-polarization to transmit 99% of the light. In a typical configuration, the larger of the two angles may be used in the devices and systems disclosed herein to ensure that 99% or more of the light is transmitted by the first optical element.

To determine the angle to reflect the excitation light, the angle should not be so large such that one of the polarizations of light is passed. For a normal incidence where the optical element blocks 99% of the light at a wavelength $\lambda_{1\% T}$, the minimum angle to block about 99% of the light may be calculated from the following equation $$\theta_{1\% T, \lambda laser} = \sin^{-1}\left(n_{eff}\sqrt{1 - \left(\frac{\lambda_{laser}}{\lambda_{1\% T, 0°}}\right)^2}\right)$$

where, again, $n_{eff}$ varies with the particular element used and is provided by the manufacturer. In this illustrative embodiment, $n_{eff}$ represents 2.08 for the s polarization, 1.62 for the p polarization, $\lambda_{laser}$ is the wavelength of the excitation source and $\theta_{1\% T, \lambda laser}$ is the angle. The angle should be smaller for the p-polarization than the s-polarization to reflect 99% of the light. In a typical configuration, the smaller of the p-polarization and s-polarization angles is not exceeded to ensure that 99% or more of the light is blocked.

Figure 3:
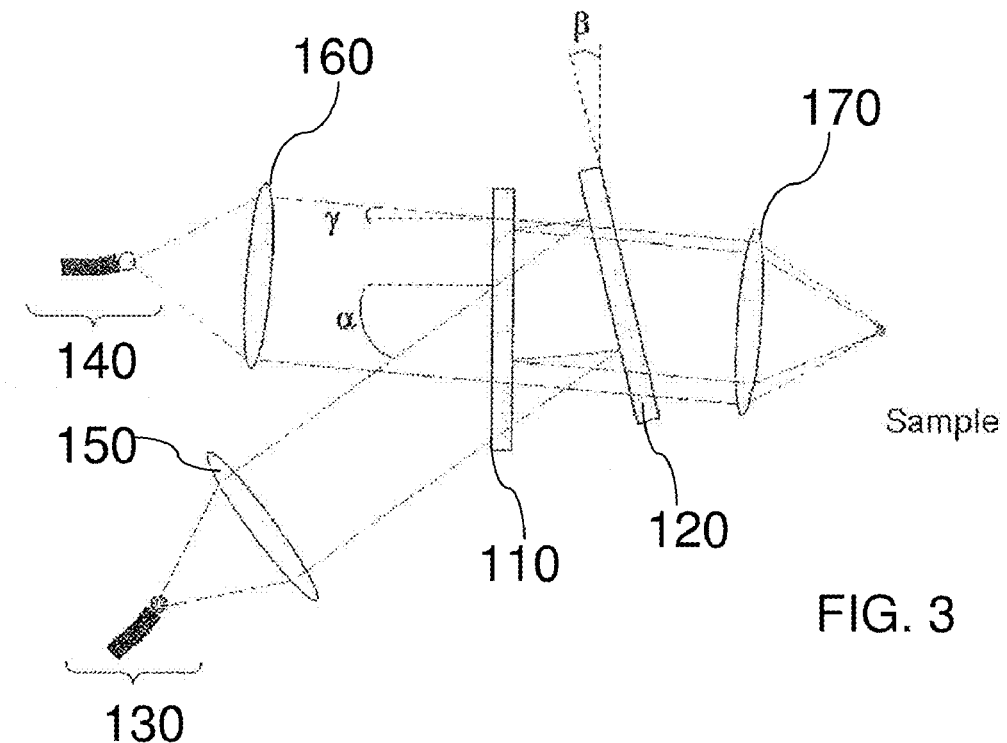
FIG. 3 is a diagram of a system comprising two long pass filters and several optical elements, in accordance with certain examples.

In certain embodiments, the particular angle of the optical elements can be expressed with reference to two orthogonal planes. A first vertical plane may be defined as being the surface of the first optical element 110, and a second horizontal plane as normal to the surface. The angle between the light source 130 and the horizontal plane is α as shown in FIG. 3. The angle between the second optical element 120 and the vertical plane is β. Also shown in FIG. 3 is a detector 140, and lenses 150, 160 and 170 which may optionally be present to focus the light. Assuming that the light source 130 is a laser, the angles can be used to express the incidence angles of the optical elements for each at the different passes. If $laser_{1,1}$, $laser_{1,2}$, $laser_{2,1}$, $laser_{2,2}$ are the angles of incidence of the laser on the first filter at the first pass, on the second filter at the first pass, on the first filter at the second pass and on the second filter at the second pass, respectively, then:

$laser_{1,1} = \alpha$ $laser_{1,2} = \alpha - \beta$ $laser_{2,1} = 2 \times \beta - \alpha$ $laser_{2,2} = 3 \times \beta - \alpha$ and for the laser to reach the sample, the angles of incidence should also fulfill the following relationships:

$|laser_{1,1}| \geq \theta_{99\% T, \lambda\, laser, s\, polarization}$ $|laser_{2,2}| \geq \theta_{99\% T, \lambda\, laser, s\, polarization}$ where $\theta_{99\% T, \lambda laser, s\, polarization}$ is the angle tuning required to transmit 99% of the s-polarization (which is the limiting factor as less angle tuning is required to transmit 99% of the p-polarization) at the laser wavelength. This insures that the laser is transmitted properly during the first pass on the first filter, and the second pass on the second filter. For improved operation, the following relationships may also be satisfied:

$|laser_{1,2}| \leq \theta_{1\% T, \lambda\, laser, p\, polarization}$ $|laser_{2,2}| \leq \theta_{1\% T, \lambda\, laser, p\, polarization}$ where $\theta_{1\% T, \lambda laser, p\, polarization}$ is the angle tuning required to block 99% of the p-polarization (which is the limiting factor as more angle tuning is possible to still block 99% of the s-polarization) at the laser wavelength. This insures that the laser is reflected properly during the second pass on the first filter, and the first pass on the second filter.

For a specific combination of angles α and β, there are several possible configurations that may be implemented. In one embodiment, for a given value of β, one value of α may satisfy the above equations such that only a single laser spot is passed to the sample. In another embodiment, for a given value of β, a range of values for α may satisfy the above equations and a plurality of laser spots may be used and placed at an angle to the horizontal plane within the range of α values. Such plurality of spots permits multiplexing using the optical devices disclosed herein.

Figure 4:
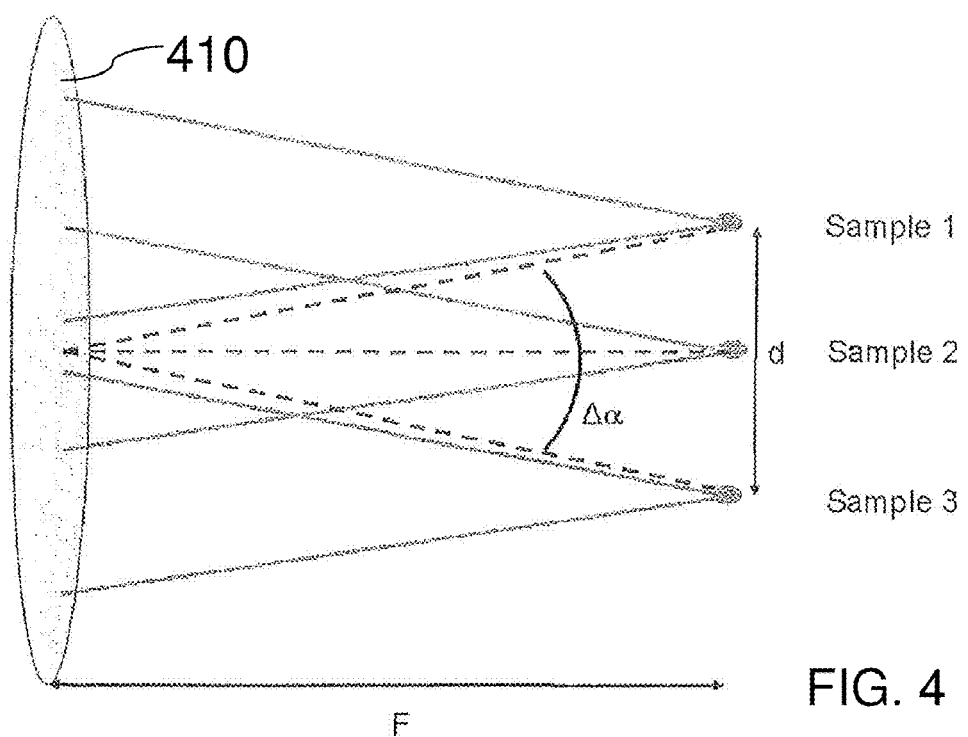
FIG. 4 is schematic of a lens and various samples, in accordance with certain examples.

In certain examples where a plurality of laser spots are used, the distance between laser spots may be selected based on the configuration of the optical elements and the exact angles used. The optical elements can either transmit the laser beams or reflect them like a mirror, neither of which will or should modify the angles between different laser beams. The position of each laser spot on the samples depends, at least in part, on the angle between the collimated laser beams and the focal length of the sample lens. By noting Δα as the maximum angle between the laser spots and F as the focal distance of the sample lens 410 (see FIG. 4), the distance d between the most distant laser spots may be found from the following equation.

$$d = 2 \times F \times \sin\left(\frac{\Delta \alpha}{2}\right)$$

In order to achieve a given value of d (for example, to have the laser spots match the spacing of the wells of a 96-well or a 384-well sample plate), the focal length F or Δα can be altered. Changing the focal length is straightforward and should not require any modification to the remainder of the system, though the optical elements may be rotated.

In some embodiments, a plurality of optical fibers may be used to provide the light and/or receive scattered or emitted light from a sample. Where a plurality of excitation fibers and a plurality of collection fibers are used, the results noted above may be counter-intuitive. The image of the array on the collection fibers is independent of any lens used for the samples. The image of the excitation array is magnified on the samples by a factor that depends on the ratio of the focal lengths of 1) the laser collimation lens and 2) the sample lens. This factor $mag_{@laser-sample}$ is expressed by $$mag_{@laser-sample} = \frac{F_{sample}}{F_{laser}}$$

where $F_{sample}$ is the focal length of the sample lens, and $F_{laser}$ is the focal length of the laser lens. The excitation array may be magnified on the samples if the sample lens has a longer focal length than the laser lens. For example, if the fibers of the excitation array are 2 mm apart, and the focal length of the sample lens is twice as much as the laser lens, the laser spots will be 4 mm apart on the samples. Similarly, the image of the sample array is magnified on the collection fibers by a factor that depends on the ratio of the focal lengths of the sample lens and any collection lens. This factor mag@sample-collection may be expressed by:

$$mag_{@sample-collection} = \frac{F_{collection}}{F_{sample}}$$

The magnification of the array of laser excitation fibers on the collection fibers $mag_{@laser-collection}$ is:

$$mag_{@laser-collection} = mag_{@laser-sample} \times mag_{@sample-collection}$$
$$= \frac{F_{sample}}{F_{laser}} \times \frac{F_{collection}}{F_{sample}}$$
$$= \frac{F_{collection}}{F_{laser}}$$

and, thus, the magnification does not depend on the sample lens.

Certain examples are described below in reference to Raman measurements. It will be recognized by the person of ordinary skill in the art, given the benefit of this disclosure, that other light emissions, such as fluorescence and phosphorescence may also be monitored using similar embodiments.

Figure 5:
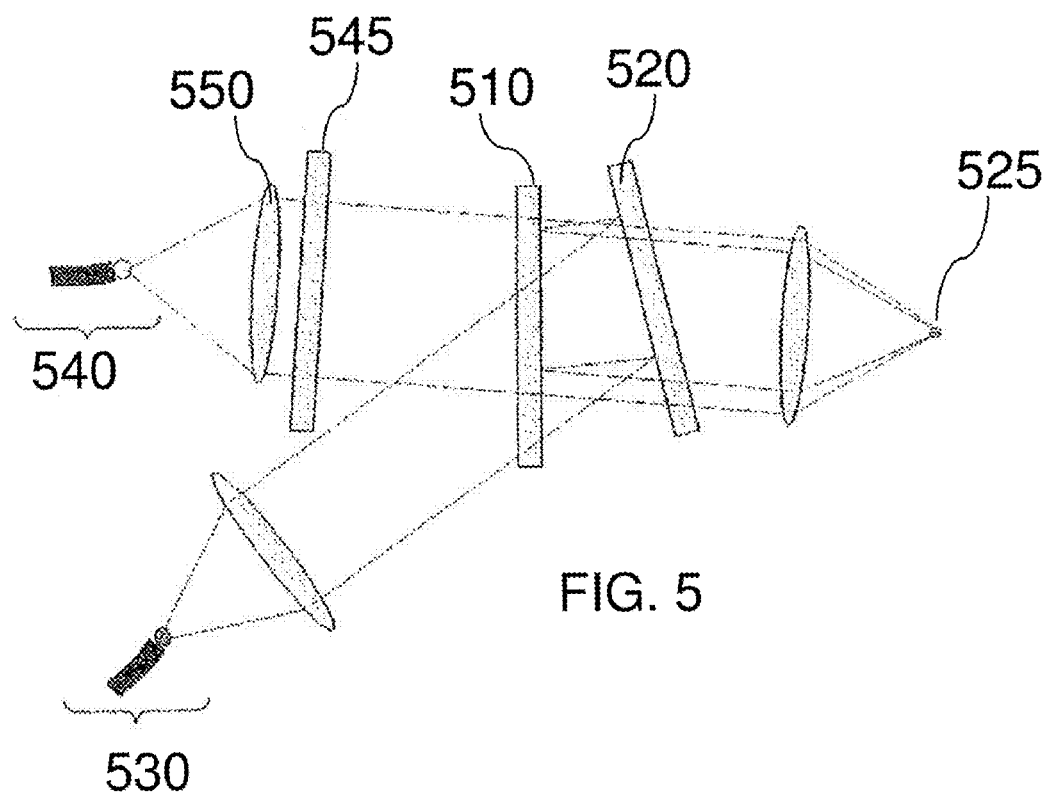
FIG. 5 is a schematic of a system with three long pass filters, in accordance with certain examples.

In certain embodiments, the devices disclosed herein may be used for measuring Raman scattering. In such instances, the collection device may be referred to as a Raman collection device or Raman collection fibers. Formation of an image of a sample array on the Raman collection fibers is straightforward. Referring to FIG. 5, if the laser spots form on the samples, then 1) the angle of incidence of the lasers on the first optical element at the second pass is small enough to block the laser wavelength and 2) the angle of incidence of the lasers on the second optical element at the second pass is high enough to transmit the laser wavelength. Since the lasers and the Raman follow the same paths, the Raman is incident at the same angles as the laser. In embodiments where the optical elements are long pass filters 510 and 520 selected based on the laser wavelength, if the filter 520 transmits the laser (pass 2), it will or should also transmit the Raman. For the filter 510, the laser is blocked at the second pass (on the way to the sample(s) 525). During the collection (coming from the sample(s) 525), the light from the laser 530 is incident at the same angles on the filter 520, so the light is blocked again and does not reach the Raman collection fibers 540. In certain embodiments, it may be desirable to include an additional optical element 545, such as a long pass filter, to block additional laser light or stray laser light. Because the long pass filters are designed to work at the laser wavelength, it follows that when they block the laser, they transmit the wavelengths immediately after the laser (red-shifted light), and the Raman is transmitted and reaches the Raman lens 550. That lens then forms an image of the sampling spots at its focal distance. Placing the collection fibers 540 in the focal plane and positioning the fibers 540 so that they coincide with the image formed results in the collection of the signals.

In accordance with certain examples, it may be desirable to increase the collection efficiency using suitable optical techniques and/or mechanical devices. While changing the sample lens will change the distance between the laser spots without requiring any modification to the rest of the elements (excitation and collection arrays, filters, laser and Raman collection lenses), it can change the efficiency of the collection. Increasing the focal length of the sample lens can be accompanied by an increase of the diameter of that lens, but because the filters and the Raman collection lens do not change size, they can act as aperture stop if the sample lens' diameter is too large. The light that does not go through the aperture is lost, reducing or eliminating the effect of increasing the lens' diameter. After going through the different aperture stops, the light reaches the Raman lens. The lens then forms an image of the sample array. Magnification of the image is independent of the lens used for the samples, and depends, generally, on the laser lens and the Raman lens. The diameter of the spots at the collection end depends on the diameter of the core of the excitation fibers and the magnification factor. When the lenses used for the laser and the Raman have the same focal lengths, the magnification factor is one, and the collection fibers desirably have at least the same core diameter as the excitation fibers but may be larger. A larger core can be used, to make the coupling easier, but a smaller core can result in loss of signal. The collection fibers can transmit the signal entering their core, for example, if the angle of coupling is within the fiber's acceptance cone.

In certain embodiments, depending on the angle of coupling, several situations can arise: the angle of coupling is larger than the acceptance angle and some of the light is not coupled properly or lost by the fiber and some of the signal is wasted; the angle of coupling is equal to the acceptance angle, and the light is coupled properly and the fiber is used at its maximum; and/or the angle of coupling is smaller than the acceptance angle, and the light is coupled properly but the fiber is under-used. With an array of fibers, some of the fibers in the array may be off the axis of the lens, so the light may not be coupled symmetrically if the fibers are parallel to each other. By changing the orientation of the fibers so that they are not parallel to each other, but face the center of the lens, the acceptance cone of the fibers can be made to match the cone of light focused by the lens. Such an arrangement provides for more efficient coupling as substantially all light from the lens may be coupled with the fibers.

In certain embodiments, it may be desirable to filter the laser light further. For example, where a plurality of excitation fibers are used to provide the laser light, the silica of the excitation fibers may generate some Raman scattering. That Raman, if not removed before it reaches the samples, will be scattered by the samples and collected as if it were originating from the sample itself, causing interference. Normally, a band pass (laser line) filter would be used for this purpose, transmitting selectively the laser wavelength (typically, a 785 am laser line filter will have its pass band between 784.0 nm and 786.0 nm). In the case of multiplex sampling however, the collimated lasers beams may not be parallel to each other so the lasers cannot be at normal incidence of the band pass filter. Using the equations above, the maximum amount of angle tuning that may be used before the filter stops transmitting the laser is about 4.7 degrees. Therefore, the maximum angle between the lasers would have to be about 9.4 degrees if a laser line filter transmitting between 784 and 786 nm, with $n_{eff}$ the same as the value used in the above paragraphs. The exact angle may vary depending on the particular laser line filter used. In general, the maximum angle between the lasers would be limited by the band pass of the laser line filter.

In certain embodiments disclosed herein, using a band pass filter is however not necessary: the filters do not transmit all light to the sample, they transmit substantially only a desired wavelength, or wavelength range, due to the angle tuning of the optical elements. For example, only the desired wavelength from a laser is transmitted, and Raman lines generated by the fiber optic of the excitation array or other wavelengths from the laser are not transmitted in substantial amounts. Qualitatively, this result may be explained by considering the different passes and each of the optical elements. The first optical element is angle tuned so that during the first pass it transmits the wavelengths that are at or equal to the laser's wavelength or longer wavelengths. Shorter wavelengths are not transmitted, but instead are blocked. The second optical element is angle tuned so that during the first pass it blocks the wavelengths that are equal to the laser's wavelength. Longer wavelengths are transmitted. The second pass on the first optical element does the same as the first pass on the second optical element—blocking the laser and shorter wavelengths and reflecting the longer wavelengths removing the Stokes Raman bands of the excitation light. The second pass on the second optical element does the same as the first pass on the first optical element—transmitting the laser and the longer wavelengths and blocking the shorter wavelengths, removing the anti-Stokes Raman bands of the excitation light. The amount of laser light collected at the same time as the Raman depends on the filtering accomplished by the optical elements. The optical density is a measure of the laser light rejection, and high values are preferred because the less laser light that enters the collection fibers, the less the silica in the fibers will generate its owns Raman signal on the way to the spectrometer. As discussed herein, the first and second optical elements are typically each long pass filters whose transmission profile is selected based on the desired wavelength of the excitation light.

In certain embodiments, two or more lenses may be used in the devices and systems disclosed herein. In some examples, the optical element closest to a collection lens may block the laser, and the other optical element (closer to a sample lens) may be angle tuned so that it transmits the laser. The optical density depends on the angle of incidence the light makes with the normal of the optical element. Since there may be several samples, signals originate from different directions and do not all make the same angle with the optical elements. The angle of incidence of the Raman has the same form as the one determined for the laser in the equations above $$Raman_{1,i} = 2 \times \beta - \alpha_i = \gamma_i$$

where $Raman_{1,i}$ is the incidence of the Raman of sample i on the first optical element, $\beta$ is the angle between the second optical element and the vertical plane, and $\alpha_i$ is the angle between the horizontal plane and the collimated laser excitation light reaching the sample i.

In accordance with certain examples, the optical fibers described herein may be used to provide a signal to the sample and/or collect a signal emitted from a sample. In some examples it is desirable to use optical fibers for their ease of use and flexibility to form them into an array. Such arrays may be configured so that an individual optical fiber receives light from an individual well in a multi-well plate or an individual spot on a chip or other device. The optical fibers may be arranged vertically and/or horizontally in many different configurations including, but not limited to grids, circles, squares or other internal or external shapes, to provide an arrangement of fibers that may be used to collect light. In operation, not necessarily all of the optical fibers will receive light from the sample. The positioning or address of the optical fibers in the collection array may be used to identify which test wells or samples emit or scatter light.

Figure 6:
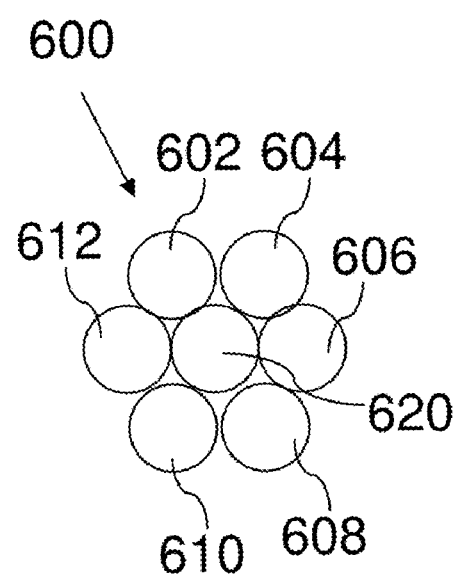
FIG. 6 is a schematic of a fiber optic bundle, in accordance with certain examples.

In some examples, a group of optical fibers may provide a single address on the collection array. An example of this configuration is shown in FIG. 6. The optical fiber bundle 600 comprises a bundle of 7 optical fibers that have been formed into a generally circular pattern with six optical fibers 602-612 adjacent to a central optical fiber 620. The six optical fibers 602-612 may function together as a slit or single aperture such that light emitted from a single test well or sample container is incident on all six of the optical fibers 602-612. The light may also be incident on the central optical fiber 620, or the central optical fiber 620 may be configured as a dead fiber to provide proper spacing between the other fibers. In other embodiments, light originating from a single well may be incident on only one (or less than all) of the optical fibers 602-612. A plurality of optical fiber bundles, such as optical fiber bundle 600 may be grouped to provide a linear (or other desired shape or pattern) array of optical fiber bundles. In operation, the optical fibers bundles that receive light show up at the detector as a track or spot.

In multiplexing operations, it is desirable that the height and width of the spot emitted by the sample is less than or equal to the overall size of the optical fiber bundle so that adjacent optical fiber bundles do not receive the same signal. As long as the image or spot is less than the height of the detector, the signal from each respective well may be imaged separately onto a detector. In the instance where the height of the image is greater than the height of the detector, the detector may be changed, for example, to one with a larger chip (the detector becomes taller), or the optics used in the wavelength analyzer may be changed to de-magnify the image of the array on the detector (the image becomes smaller), or both, thereby making the image fit on the detector. In addition, optical fibers with a thinner cladding may be used to reduce the height of the image, without changing the efficiency of the system, or optical fibers with a smaller core may be used.

Figure 7:
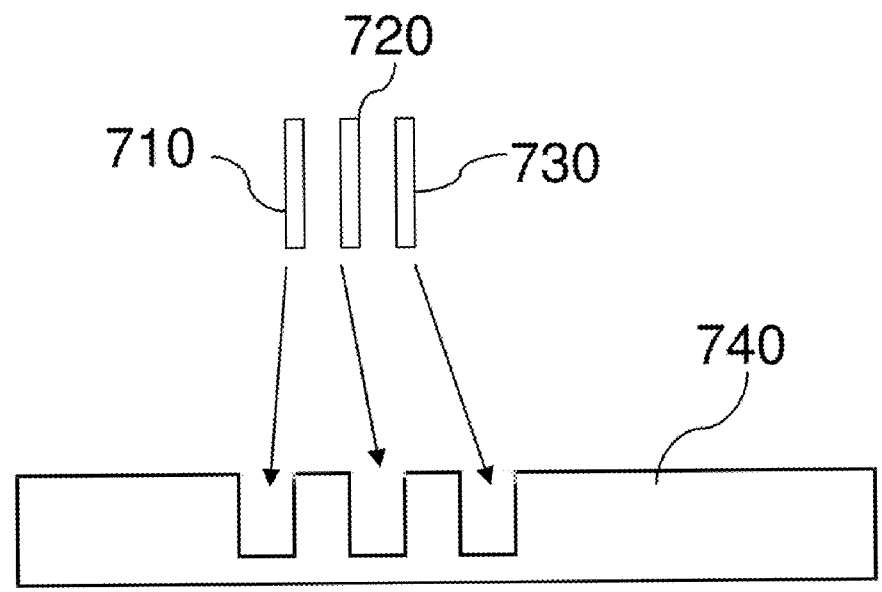
FIG. 7 is a schematic of three fiber optic apertures providing light incident on a well plate, in accordance with certain examples.

In certain embodiments, an optical fiber bundle may be used to provide a plurality of laser spots to the optical elements, which may be configured to position the laser spots separately on wells in a multi-well plate. For example, an optical fiber bundle may include a plurality of optic apertures each configured to provide a single spot or beam of light to the optics and onto a sample. Each of the spots may be incident on a single well or site of a sample such that individual wells or sites receive their own spot or beam of light. Wells that scatter the light, or emit light in the case of fluorescence or phosphorescence, may show up as spots at a collection fiber optic bundle. In some examples, each optical fiber of the collection bundle may be optically coupled to a respective well or site of the sample such that scattering or emission from different areas of the sample may simultaneously be received by the detector. An illustrative embodiment is shown in FIG. 7. Shown are three optical fiber apertures or ferrules 710, 720, and 730 of an optical fiber bundle. The optical elements (not shown) may be angle tuned such that each beam or spot of excitation light from the apertures 710, 720 and 730 is incident on a single well in a multi-well sample device such as, for example, a multi-well plate 740.

In certain examples, the collection optical fiber bundle may be optically coupled to a detector such as a charge-coupled device (CCD), photomultiplier tube or the like. In certain embodiments, the detector is a CCD such that multiple light emissions or light scattering measurements may be detected simultaneously. When a CCD is used, the emission spots from individual samples may show up as tracks on the CCD detector with various resonance lines being displayed for each sample.

In certain examples, a system comprising a device configured to provide light to a sample is provided. In some examples, the system may further comprise a first optical path between the device configured to provide the light and the sample. In other examples, the system may further comprise a first optical device in the first optical path that is configured to pass light received from the device configured to provide the light. In certain embodiments, the system may also include a second optical device optically coupled to the first optical device, the second optical device configured to reflect incident light from the first optical device back to the first optical device and to pass the light reflected from the first optical device to the sample. In other embodiments, the system may include a device configured to detect light emitted from the sample, e.g., a detector, wherein said device is optically coupled to the sample through a second optical path and wherein the first optical device and the second optical device are in the second optical path and are configured to pass emitted or scattered light from the sample to the detector along the second optical path.

In certain examples, the device configured to provide light comprises an optical fiber bundle optically coupled to a laser. In certain embodiments, the first optical device and the second optical device may each be a long pass filter. In other embodiments, the device configured to detect light comprises an optical fiber bundle optically coupled to a charge-coupled device. In other examples, the system may further include at least one additional optical device.

In certain examples, a method of providing light to a sample comprising angle tuning at least one optical element is provided. In certain examples, two or more optical elements may be angle tuned such that a first optical element is configured to pass light received from an excitation source, a second optical element is optically coupled to the first optical element and is configured to reflect incident light from the first optical element back to the first optical element and configured to pass the light reflected from the first optical element. Additional optical elements may also be used to provide the light to the sample.

In other examples, a method of detecting emitted or scattered light comprising configuring a system with at least one angle-tuned optical element is disclosed. In some examples, the system may be configured with first and second angle-tuned optical elements that pass light from a sample to a collection device such as, for example, a charge-coupled device optionally optically coupled to an optical fiber bundle. Additional optical elements may also be used to detect the light emitted or scattered by the sample.

In certain embodiments, a method of multiplexing is disclosed. In some examples, the method comprises simultaneously detecting at least two spots or beams of scattered or emitted light by passing the scattered or emitted light through at least one angle tuned optical element. In some examples, the scattered or emitted light may be passed through two or more optical elements that have been angle tuned. For example, two or more angle tuned long pass filters may be used in the multiplexing methods.

Certain specific examples are described below to further illustrate the novel and non-obvious technology described herein.

EXAMPLE 1

Optical Fiber Selection

Figure 21:
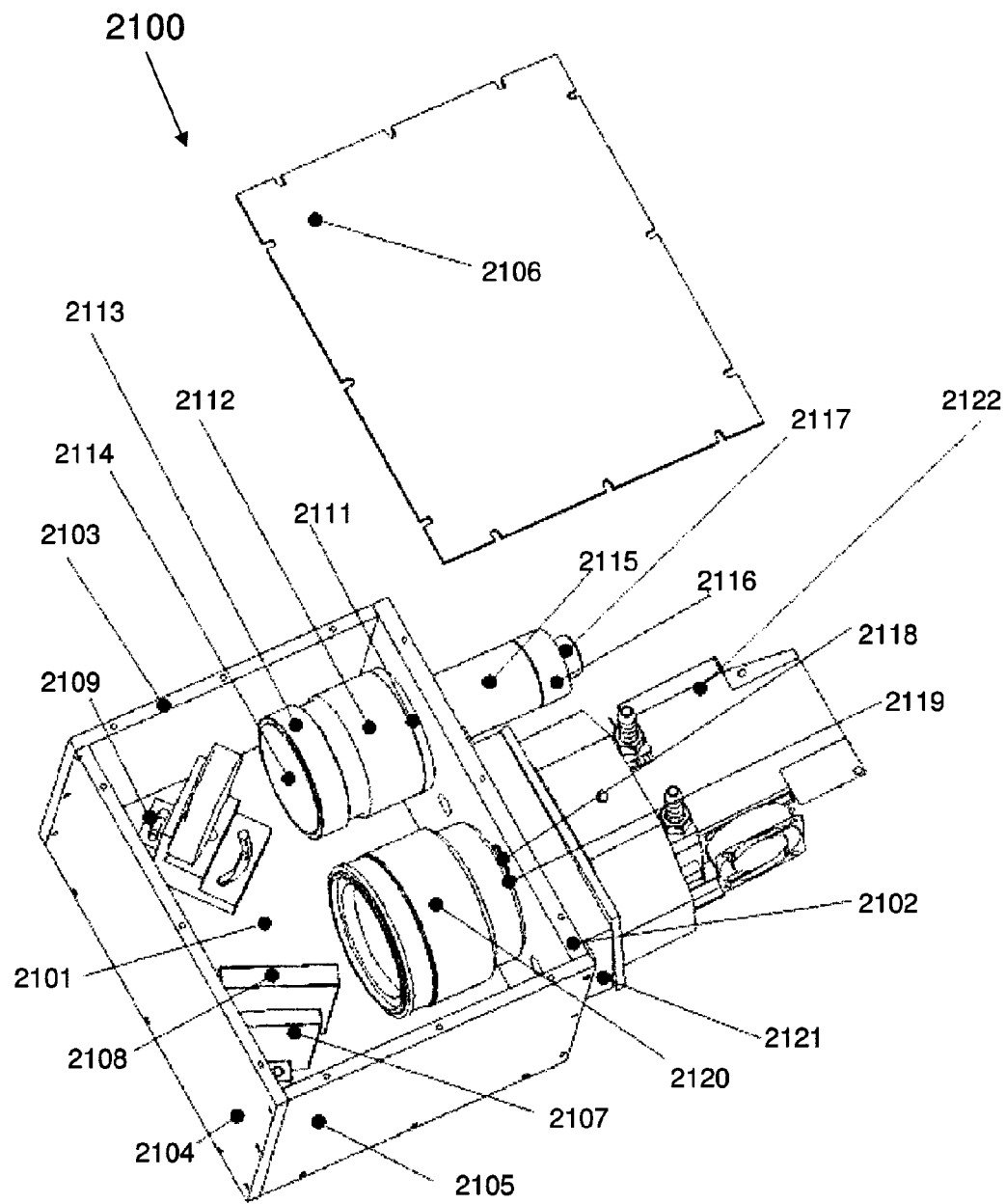
FIG. 21 shows a schematic of a spectrometer, in accordance with certain examples.

Filters for use in an optical device configured to collect signal from six samples simultaneously were selected. Two custom optical fiber bundles were manufactured—the first one for the excitation light and the second one for the signal collection. The optical fiber bundles were designed to achieve a spacing of 4.5 mm between the laser spots (to roughly match the well spacing of a 384-well plate) by using an available 785 nm laser source, and two 785 nm long pass filters (25 mm diameter), and a spectrometer as used in commercially available PerkinElmer Raman instruments capable of 785 nm excitation. A schematic of the spectrometer is shown in FIG. 21. The spectrometer 2100 included a base 2101, walls 2102, 2104, and 2105, a lid 2106, a grating mount 2107, a grating 2108, a mirror mount 2109, a lens mount 2111, a lens tune 2112, a lens adjuster 2113, a lens 2114, a ferrule tube 2115, a ferrule mount 2116, 2117, a lens lock 2118, a lens hood 2119, a lens 2120, a detector mount 2121 and a detector 2122. The focal length of the lens used for the collimation of the lasers was chosen so that the filters would transmit both polarizations of all six laser beams.

Figure 8:
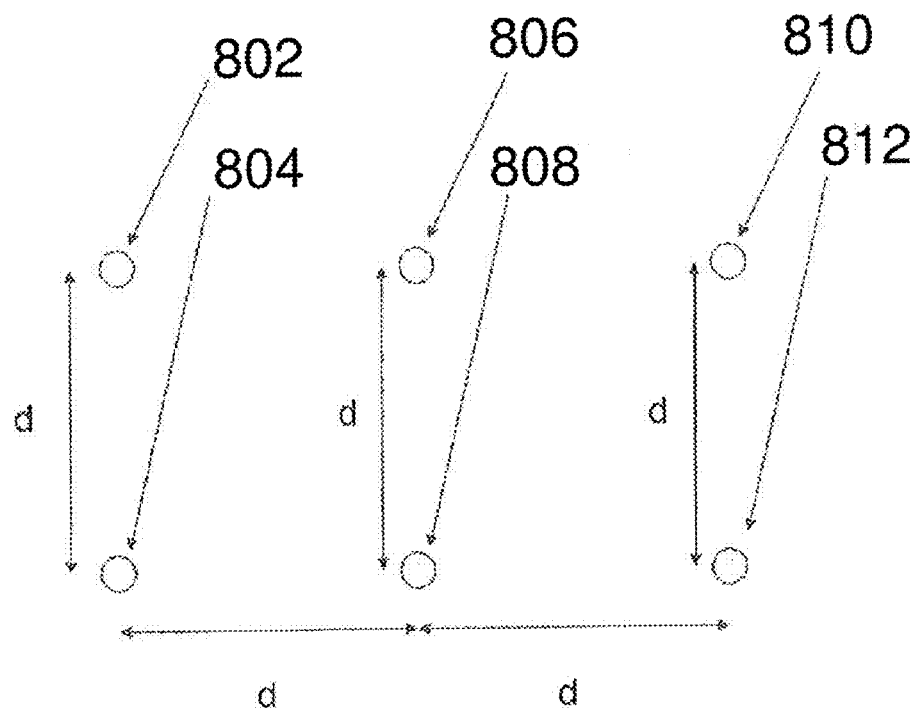
FIG. 8 is a schematic showing a fiber array having two rows and three columns (2×3 array), in accordance with certain examples.

To minimize the focal distance of the lens used to focus the laser on the samples while achieving the desired 4.5 mm separation between the laser spots, the angles between the different laser spots was selected to be as large as possible. However, the angles also were selected to not be so large that the filters would start to fail at sending both polarizations towards the samples. With the filters used, applying the equations above provided a maximum angle of incidence on the filters of 11.1 degrees to provide 99% or more reflection of both laser polarizations. Similarly, a minimum angle of 15.9 degrees was calculated to be necessary to provide 99% transmission of the laser (both polarizations). The combinations of angles $\alpha$ and $\beta$ were used, and the angle $\beta$ found to give the largest range of angles $\alpha$ verifying the equalities was found to be $\beta=-14°$. The range of $\alpha$ was 25° to 17° (i.e. 21°, +/−4°), so the filters would work with angles of incidence over a range of 8 degrees. The number of optical fibers to be used in the array was selected to be six, a compromise between using more fibers (which may require more expensive bundles) and using fewer fibers (not enough to utilize the multiplexing advantage of the device). The fiber array was configured to match the well arrangement of a sample plate and was arranged in two rows of 3 fibers each. Referring to FIG. 8, the six fibers 802, 804, 806, 808, 810, 812 and 814 were arranged in three columns and two rows (a 2×3 array). Each of the fibers in the rows was separated by a distance d, as shown in FIG. 8, and each of the fibers in the columns were also separated by the same distance d.

The maximum angle between the lasers, covering a range of 8 degrees, is reached between the fibers in opposite corners of the array. The distance between those fibers is the square root of 5 times d, and the distance to the lens is the focal length, $F_{laser}$. The following relationship was used to verify proper functioning.

$$d = \frac{2 \times F_{laser}}{\sqrt{5}} \times \tan(4)$$

The focal length $F_{laser}$ was selected so that it was not so large that the light exiting the excitation fibers produced a cone too wide to be fully captured by the lens. The following equation was used to express the maximum focal length as a function of the fiber's distance to the lens' optical axis $$F_{laser} \leq \frac{D_{laser}}{2 \times (\tan 4° + \tan(\theta))}$$

In the above equation, $D_{laser}$ is the diameter of the lens used to collimate the laser excitation, $F_{laser}$ is its focal length and $\theta$ is the acceptance angle (half of the acceptance cone) of the fiber. The lens mounts used in the set up were designed for 25 mm optics, and the clear aperture was slightly less (about 22 mm) because of the fixation mechanism. Therefore $D_{laser}=22$ mm. The fibers used had an acceptance angle of 12.7° (NA=0.22) so the maximum focal length that could be used for the collimation of the laser in this setup was 37.3 mm. The closest focal lengths commercially available were 35 mm and 30 mm. A 30 mm lens was selected, to provide some leeway is case the array was not centered properly with reference to the lens' optical axis. With a 30 mm focal length, a value of 1.9 mm may be used between the fibers in the array to have 4 degrees between the outermost fibers (in opposite corners). Two 30 mm lenses were used, one for the laser collimation and one for the Raman collection. Having two lenses of equal focal lengths provides a magnification of 1.

Two custom fiber bundles were used, one for the excitation and one for the collection. The fibers were ordered from Fiberguide Industries (Stirling, N.J.). The excitation bundle had a 6 around one arrangement at one end (6 excitation fibers around 1 unused central fiber), and the 6 fibers were rearranged at the other end into a 2×3 array, with 1.9 mm between the different fibers. The collection bundle had a similar array at one end, and at the other end the fibers were aligned into a slit with a gap of 0.5 mm between the different fibers so that each would give a track well separated from the others on the detector.

EXAMPLE 2

Alignment of Optical Components

A prototype device was assembled by using each of the bundles of Example 1 with a 30 mm lens, two 785 nm long pass filters, a 785 nm laser and a 70 mm lens for the samples. The 70 mm lens provides a distance between the laser spots matching the spacing between the wells of the 384 well plate.

To place the excitation array in focus, one end of the fiber bundle (the 6 around 1 end) was coupled with the laser so that each of the fibers would receive comparable amounts of laser power. The 6-around-1 fiber bundle was mounted on an x-y-z micrometric stage. A lens (7.5 mm focal length) was used to focus the beam of a Torsana 785 nm laser. The focused spot was smaller than the fiber bundle, so the fiber bundle was placed off focus using the z-axis control. The array was moved along the x- and y-direction to have similar (but not equal) laser power coming from the 6 used fibers (the 6 focused laser spots had similar brightness). The other end of the fiber bundle (the 2×3 array) was placed in front of a 30 mm lens, and moved at a distance such that the diameter of each of the collimated lasers would be constant over a distance of about 10 meters. The collection array was placed at the focal distance of the other 30 mm lens in the same way, with the difference that an incandescence bulb was used as a light source, and not a laser, to select the exact position of the collection array.

Figure 9:
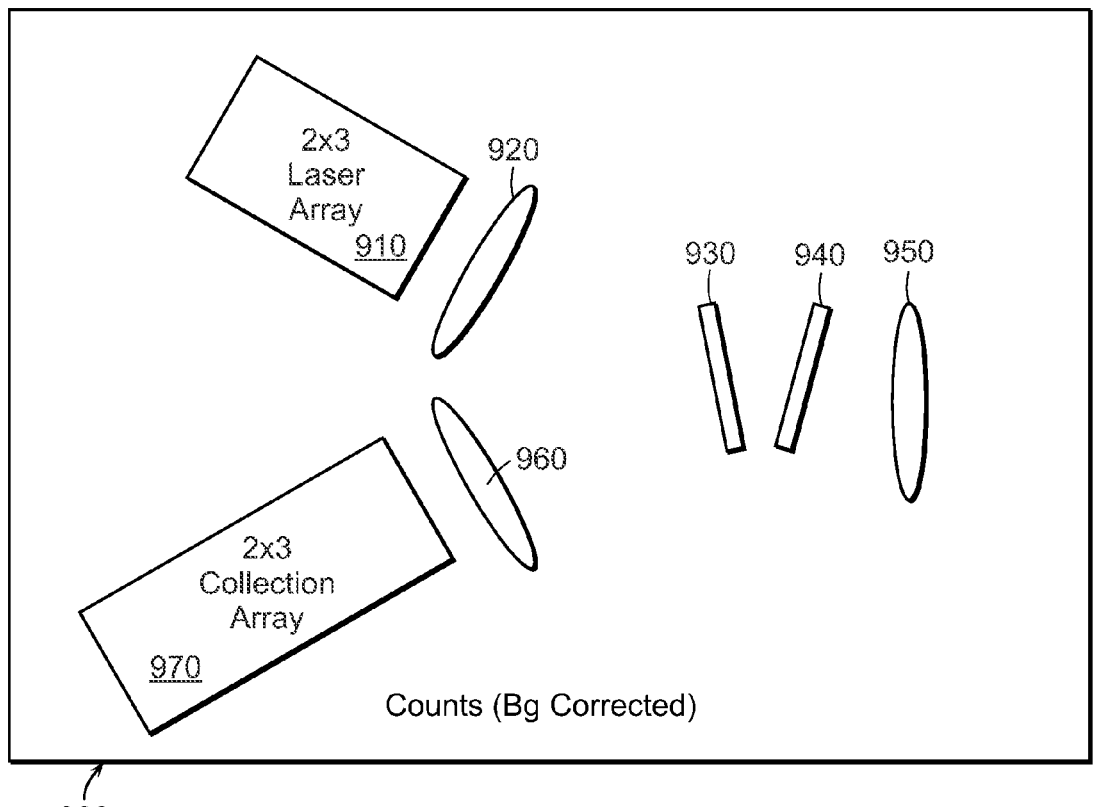
FIG. 9 is a diagram of a spectroscopic system, in accordance with certain examples.

The excitation and collection bundles, together with their lenses and the 70 mm lens, were then placed on an optical bench. At this stage, the filters were not added to the system. The white light from the collection array was focused by the 70 mm lens providing six spots of white light on a target placed at the lens' focal distance. In order to align the laser spots with the collection spots (made visible by the white light), the filters were inserted. With filters from one supplier, the spots mostly disappeared because the filters were blocking most of the white light (shorter wavelength than 785 nm) but faint green spots were still visible, because these filters had some transmission in the green wavelengths. With filters from another manufacturer, the spots disappeared completely, because the transmission was very low at all the wavelengths shorter than 785 nm. The first set of filters were Semrock 785 U long pass filters, and the second set of filters were Iridian 785 nm long pass filters. A diagram of the system is shown in FIG. 9. The system 900 included a 2×3 laser array 910 optically coupled to a 30 mm lens 920. Filters 930 and 940 and a 70 mm sample lens 950 were also optically coupled to the laser array 910. A 2×3 collection array 970 was also optically coupled to the filters 930 and 940 and the 70 mm lens 950. Another 30 mm lens 960 was positioned between the collection array 970 and the filters 930 and 940. The relative distances and sizes of the components shown in FIG. 9 are not shown to scale. Generally, all of the components were in the same plane, so there was no vertical spacing. The lens in front of the excitation array was about 4 cm away from the first filter. The lens in front of the collection array (connected to the spectrometer) was about 6 cm away from the first filter. To align the laser spots with the collection spots, the filters were rotated so that both polarizations of the six lasers were transmitted to the sample lens such that six laser spots were formed. To find the correct angle combinations, the angles between the filters were changed, and then the two filters were rotated together. The ferrules of the laser and collection arrays were also rotated so that the spots were in the same direction.

Some of the combinations successfully resulted in six laser spots forming on the samples, but not where the six collection spots were. The angle combinations could result in the spots too far to one side of the collection spots, or too far to the other side. By having the right angles between a) the two filters and b) the first filter and the optical axis of the laser lens, the laser and collection spots were matched horizontally (for fine adjustments in the horizontal plane, the x-adjusters of the ferrule mounts were used). The height of the spots is generally independent of the filters, so to have the laser spots vertically aligned with the collection spots, the y-adjusters on the ferrule mounts were used to change the position of the arrays relative to the lens in the vertical plane, hence the direction of collimation and the angle of incidence on the sample lens and the height of the focusing. Moving the ensemble of the lens and the array together did not change the focusing height because the angle of incidence on the sample lens did not change and it is that angle, not the position where the light enters the lens, that affected the focusing height.

EXAMPLE 3

Data Collection

The collection bundle was connected to the entrance of the spectrometer, which is shown schematically in FIG. 21, then aligned vertically and brought to the focal distance of the collimation lens by placing a neon source with a diffuser near the focal plane of the sample lens. The laser was then turned on, and six different samples were placed in front of the six laser spots. The samples were varied and included a pharmaceutical tablet (sample 1), a pigment (sample 2, $TiO_2$) and polymers (polystyrene, polypropylene and polyethylene).

An image of the detector was then taken, showing the spectra of the different samples as six distinct tracks. The height of the image occupied approximately two thirds of the detector, with wide gaps between the tracks corresponding to the spacing between the fibers on the slit. The tracks were not perfectly centered on the detector because the detector had not been adjusted, but this did not affect the data in any way. The dispersion occurred in the horizontal plane. An image from the detector is shown in FIG. 10.

Figure 10:
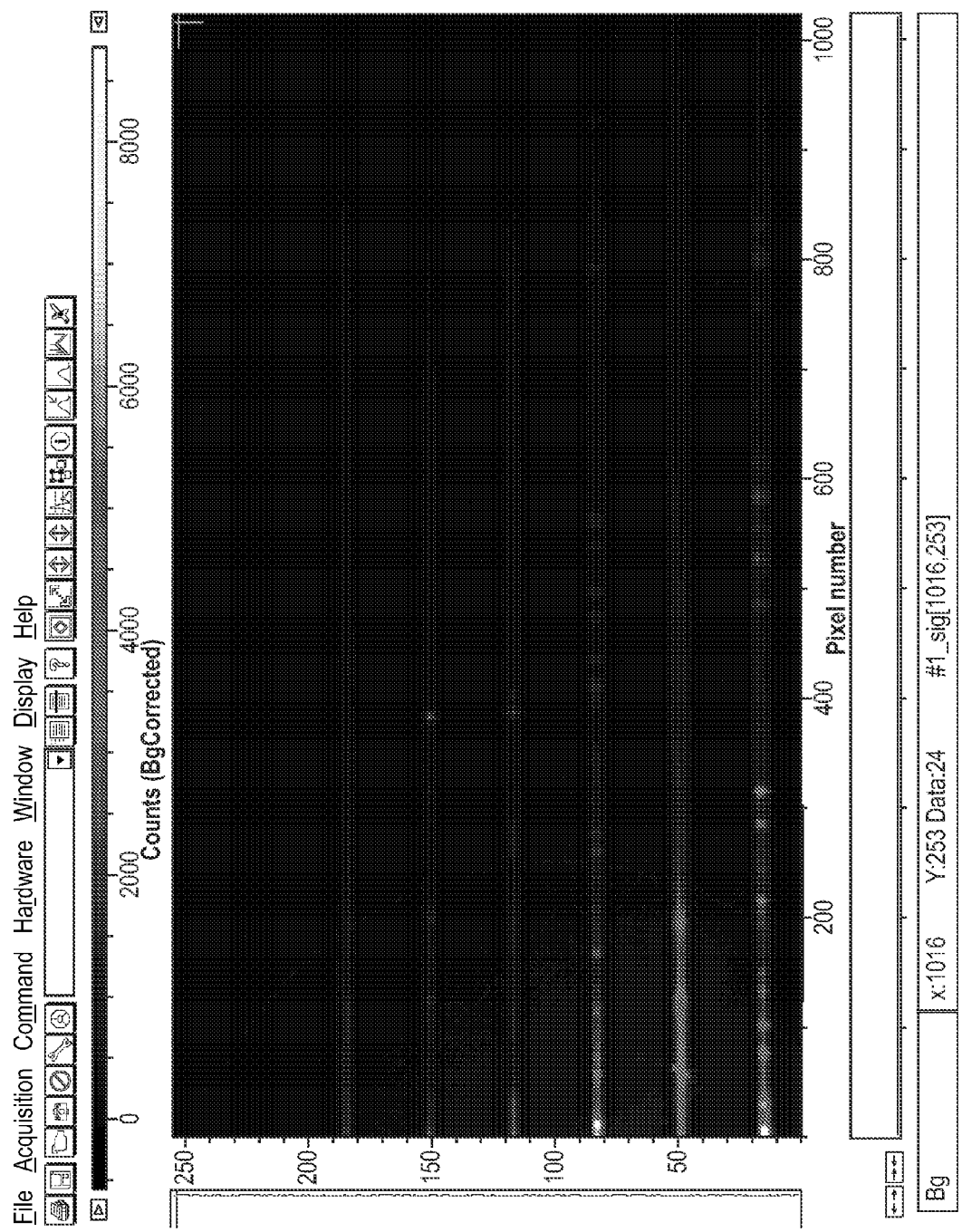
FIG. 10 is an image on a detector, in accordance with certain examples.
Figure 11:
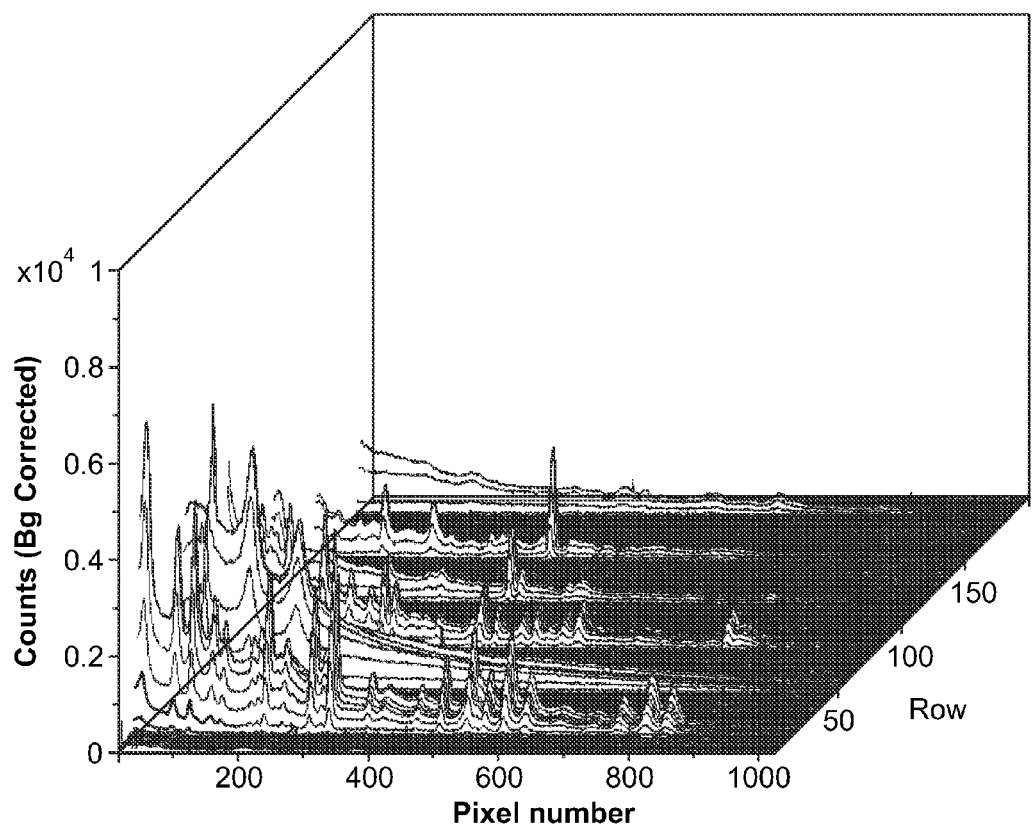
FIG. 11 is a visualization of FIG. 10 showing sample tracks, in accordance with certain examples.
Figure 12A:
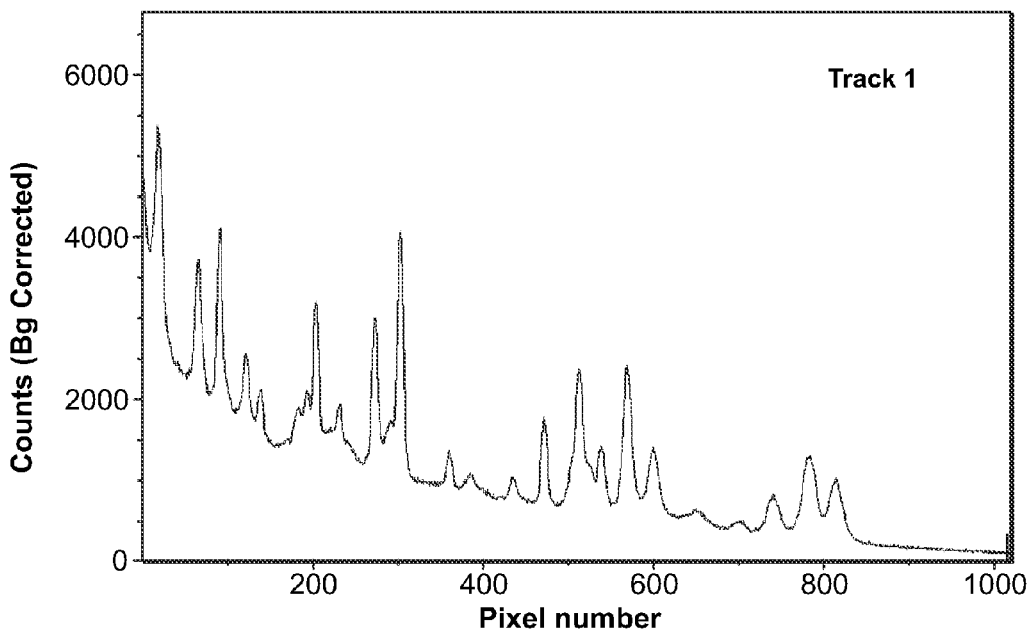
FIGS. 12A-12F is a visualization showing separate tracks, in accordance with certain examples.
Figure 12B:
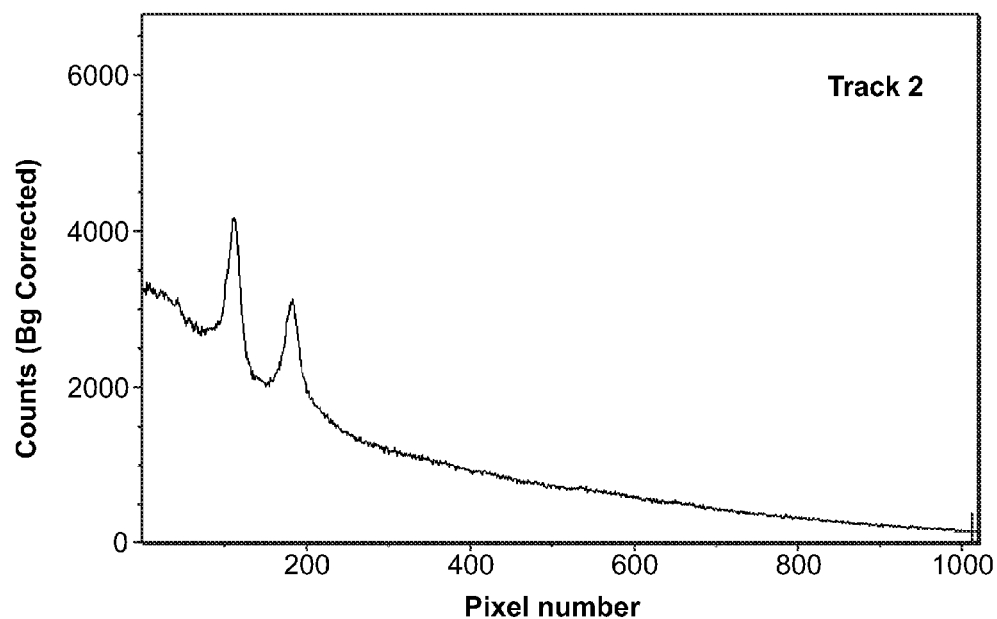
Figure 12C:
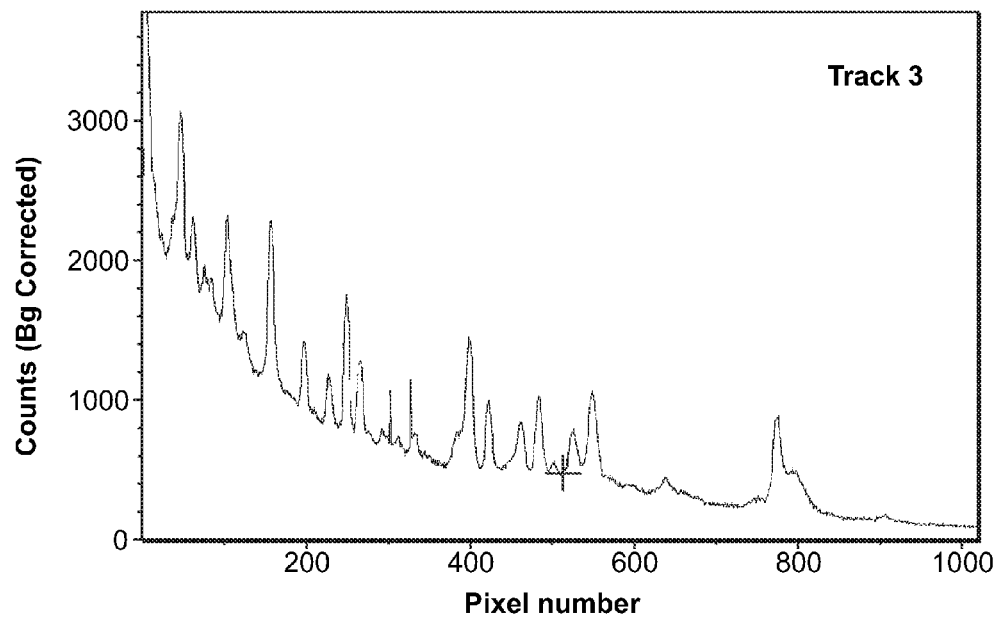
Figure 12D:
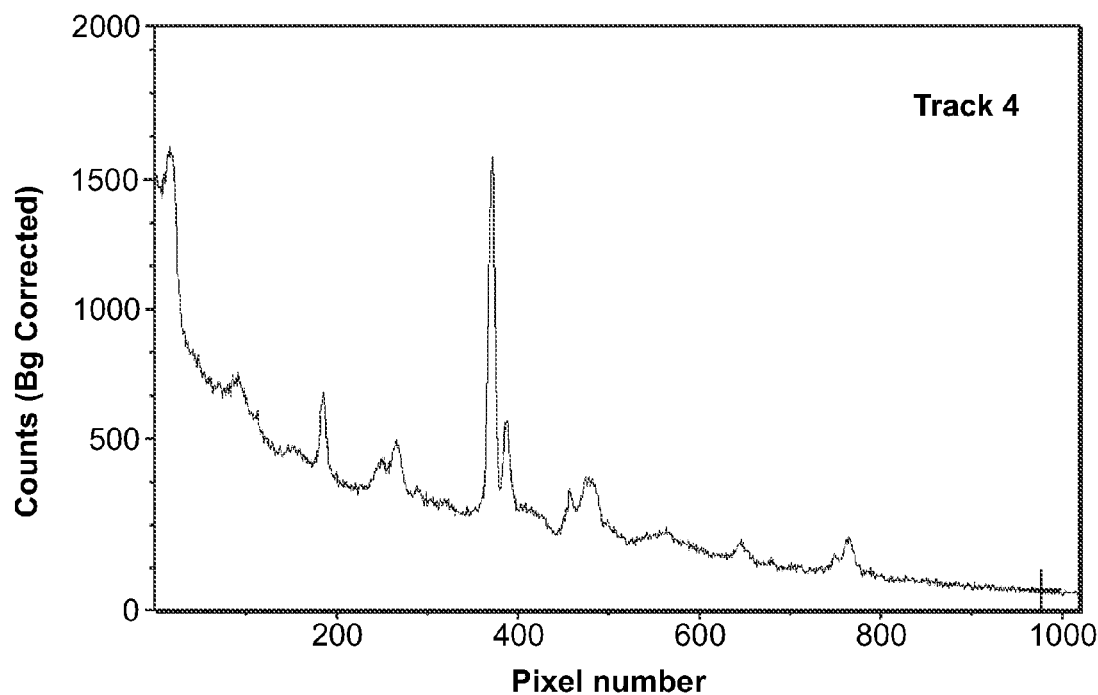
Figure 12E:
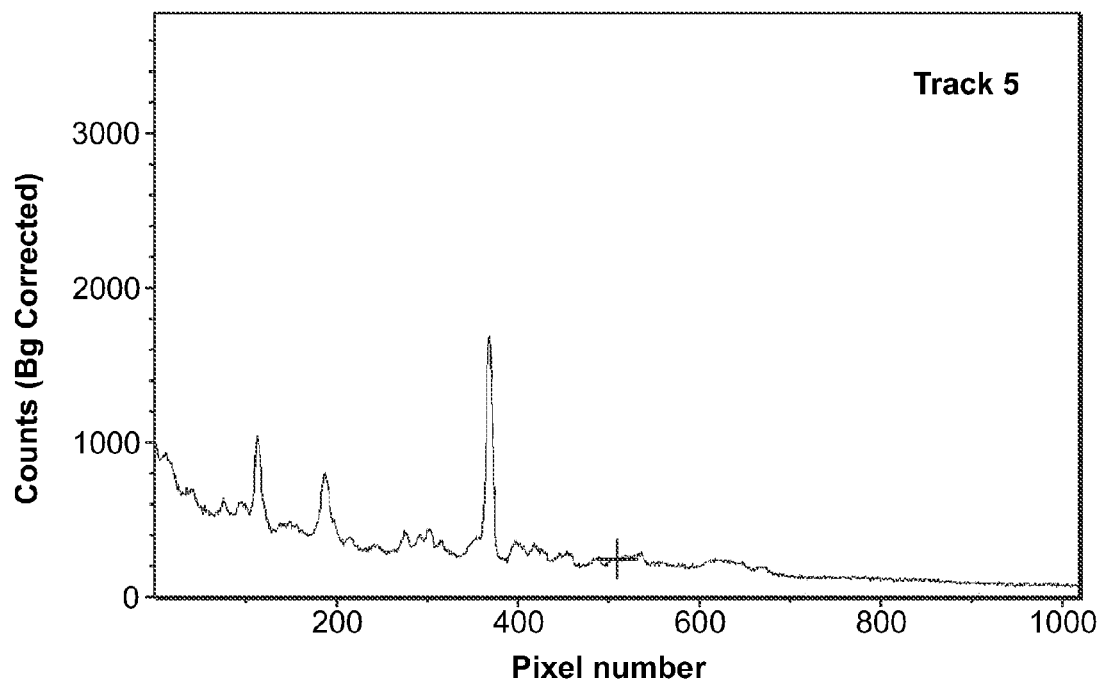
Figure 12F:
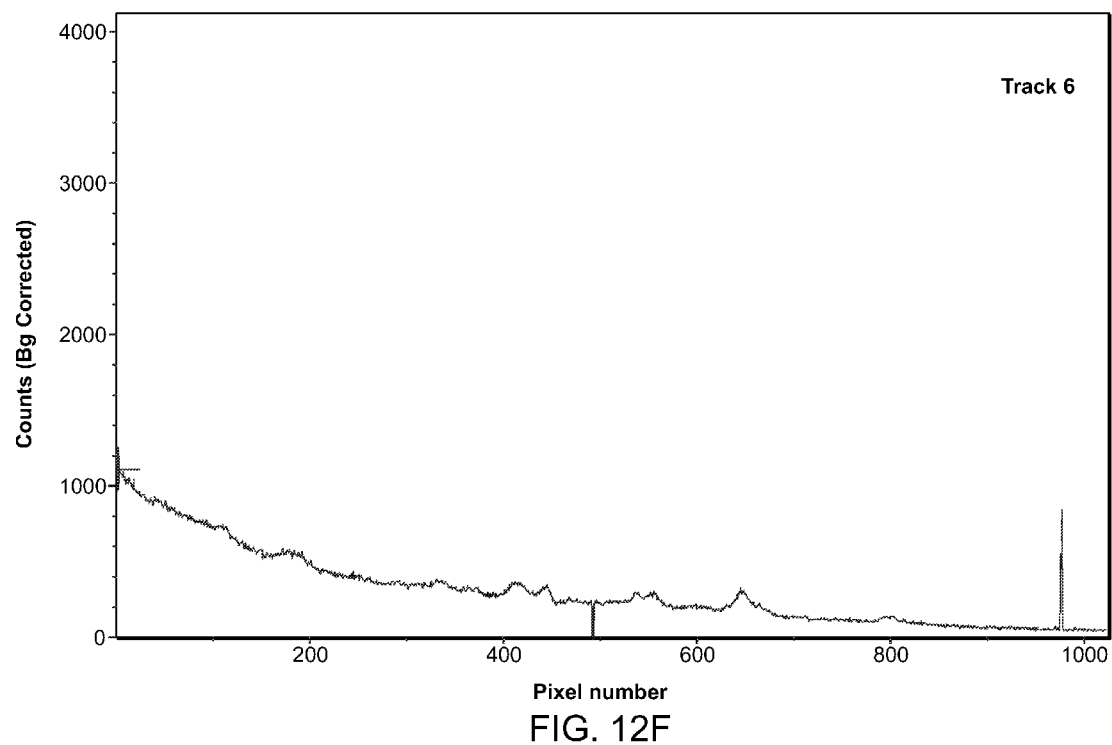

The image shown in FIG. 10 can also be visualized in a different manner, where each row of pixels from the image is shown as a separate spectrum. The resulting visualization (FIG. 11) shows the sample tracks are series of stacked spectra, and the gap between the tracks are a flat "floor" from which the spectra emerge. The differences in the Raman bands (position and intensity) between the samples are easier to see with the data presented in this manner.

A third way of visualizing the spectra is shown in FIGS. 12A-12F, where background corrected counts versus pixel number are plotted. In this configuration, the detector is configured for multi-track operation, a feature which bins the data over a specific (user defined) number of rows grouped in a track. The rows corresponding to the different tracks are determined in the image of the detector (FIG. 10), and the output of the software is six spectra (one per track). Because the data for each spectrum is the binning of several rows of pixels, there is less noise on the data compared to the other two visualizations.

The device described above permits acquisition of data from several samples simultaneously with the same system. The multiple signals can then be analyzed simultaneously with a suitable system. The prototype built and tested demonstrates the feasibility of a multiplex system based on this design. The cost of producing the design is less than having a separate laser and/or collection device for each point. Similarly, by using several lasers (one per sample) or a high power laser (shared among the samples), a Raman spectrometer using the multiplex design can acquire spectra from many samples in very little time.

EXAMPLE 4

Inline Sampling Optics

The novel design described in Examples 1-3 advantageously uses a difference in the angle of incidence of the laser and the Raman on two angle tuned filters to align the paths of the laser with the Raman's path. In order to achieve that difference of incidence, two lenses were used, one dedicated to the laser and one dedicated to the Raman, and the lenses were placed side by side.

Figure 13:
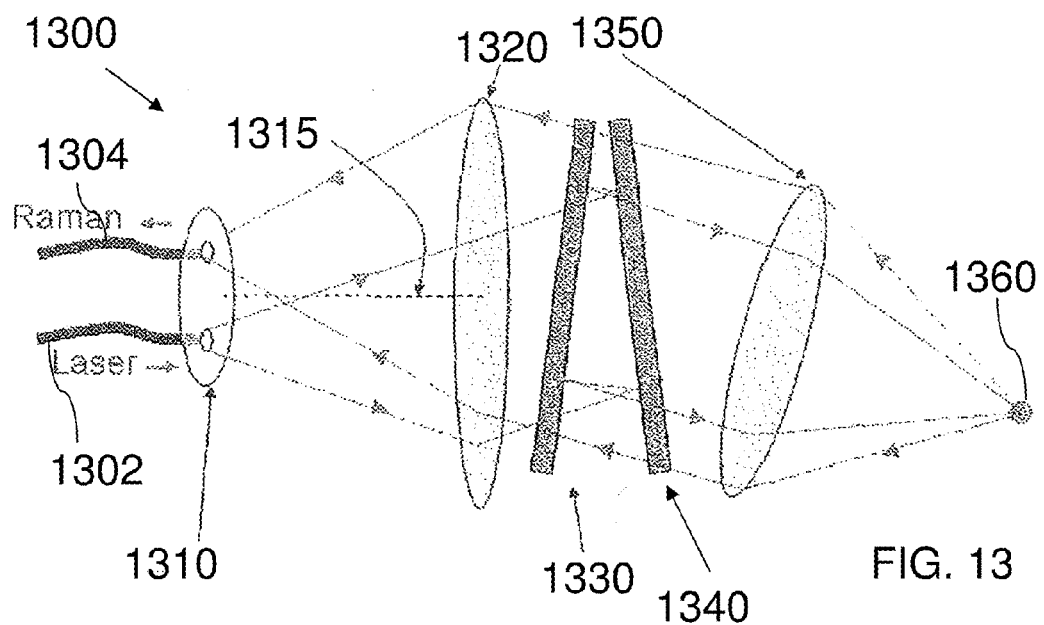
FIG. 13 is one arrangement of in-line sampling optics, in accordance with certain examples.
Figure 14:
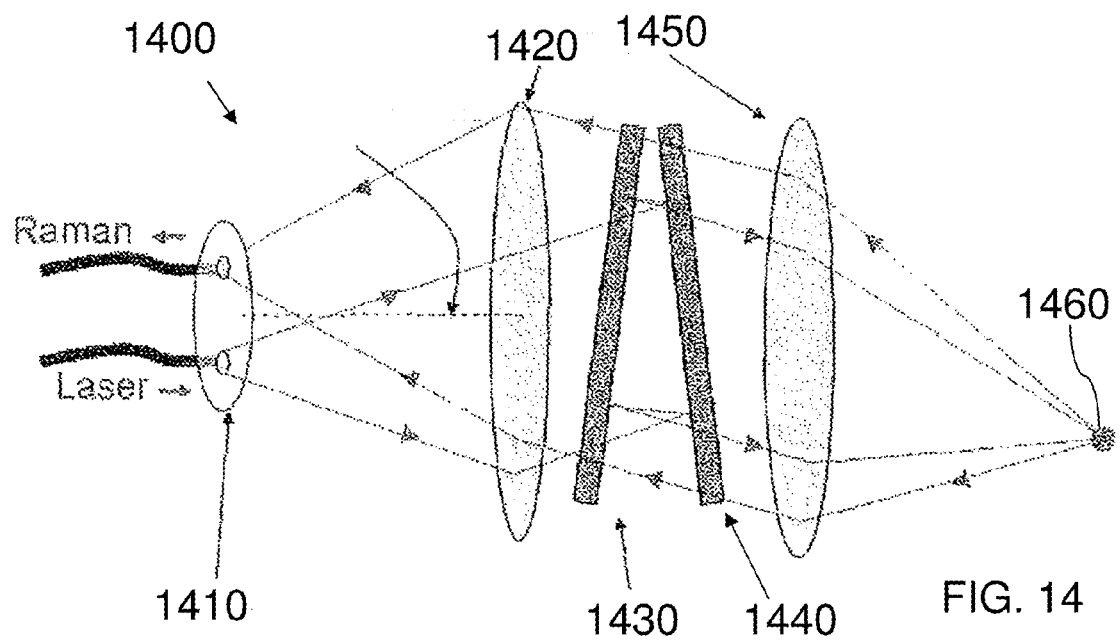
FIG. 14 is another arrangement of in-line sampling optics, in accordance with certain examples.

The difference of incidence on the filters can also be achieved by using a single lens for both the laser and the Raman. In order to do so, the fibers may be placed off the optical axis because the direction of collimation depends on the fiber's position relative to it. The resulting size of the system (or a module) is much smaller than in prior systems, because all the elements are aligned together; there is no lens on the side. FIGS. 13 and 14 show two possible arrangements of the optics, which can be very close to each other in both cases. As shown in FIGS. 13 and 14, the optical elements are angle tuned to provide the desired optical properties for the system. Referring to FIG. 13, the device 1300 comprises a ferrule 1310, a first lens 1320, first and second angle tuned filter elements 1330 and 1340, and a second lens 1350. The device 1300 is shown as focusing laser light on sampling point 1360. By placing the laser excitation fiber 1302 and the Raman collection fiber 1304 off the optical axis 1315 of the same lens, the angles of incidence of the collimated beams on the angle tuned filters are different. The laser is redirected in the path of the Raman, thereby aligning the Raman collection spot and the laser excitation spot together.

Referring to FIG. 14, the device 1400 comprises a ferrule 1410, a first lens 1420, first and second angle tuned filter elements 1430 and 1440, and a second lens 1450. The second lens 1450 is substantially parallel to the collimating lens 1420. The device 1400 is shown as focusing laser light on a sampling point 1460. In this arrangement, the sampling point does not move, but the lens will exhibit more aberrations because the light is off-axis and off-center. More than one sampling point can be achieved by using arrays of optical fibers for the excitation and collection.

EXAMPLE 5

Laser Filtration

Angle tuning of the two optical elements, e.g., the two long pass filters, permits the laser wavelength to reach the sample.

With the inline optics, the lens collimating the laser(s) and focusing the Raman is placed before the filters, so some of the light coming from the excitation fibers (laser and Raman from the silica) is scattered by the lens, and some of the scattered light is then collected by the Raman collection fibers. This result may be detrimental to the quality of the Raman spectrum of the sample(s) as the Raman spectrum of the fibers will be overlaid with it.

To avoid this result, in some embodiments a laser line filter can be placed directly in front of the excitation array to selectively transmit the laser wavelength towards the collimation lens. While this does not prevent scattering of the laser, it stops or reduces the Raman of the silica excitation fibers from reaching the lens, and therefore from being scattered and collected by the collection fibers. The scattered laser can be prevented from entering the collection fibers by a number of ways.

In order for the device to have good performance, it may be desirable to increase the filtering of the laser light. Several methods can be used for this purpose. In one method, an optical fiber bundle with a built in Bragg grating may be used. By using a Bragg grating, built in the fiber core itself, the laser wavelength is selectively prevented from being carried by the fiber. In another method, the tip of the fiber may be coated with a filter. By coating the tip of the fiber with a filter, the collection of laser light by the fiber is prevented. In yet another method, a long pass filter may be placed directly in front of the collection array. Using a long pass filter placed directly in front of the Raman collection array works according to the same principles, but the filter's optical density will not be at its maximum. These three approaches have the advantage of not letting the laser light inside the fiber, so there is no possibility for the silica of the fiber to generate its own Raman spectrum while it carries the Raman spectrum of the sample to the spectrometer. Filtering the laser at the other end of the fiber may, in contrast, make it possible for the silica to produce interfering Raman (but not a lot because only a fraction of the laser power is collected). It will however prevent the laser from entering the spectrometer and therefore stray light will not be an issue.

EXAMPLE 6

Prototype Device with In-Line Optics

Figure 15:
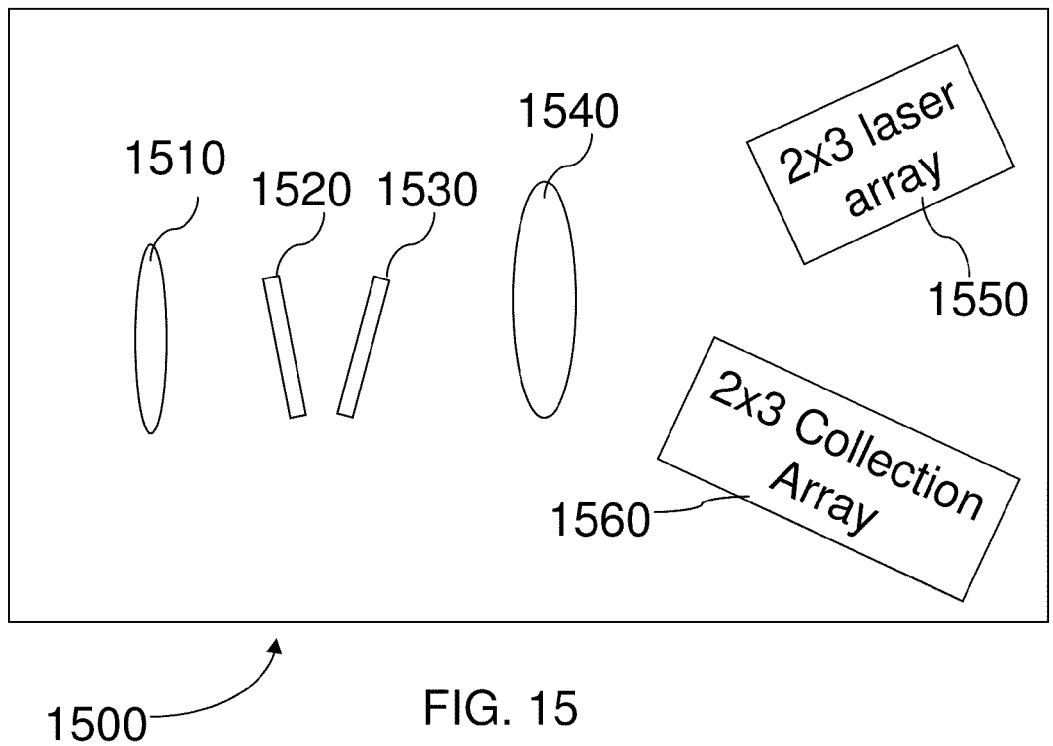
FIG. 15 is a diagram of a system that includes an imaging lends, in accordance with certain examples.

A prototype of a device using in line optics was built to verify the feasibility of this configuration. The prototype was made using the same laser, the same fiber bundles and the same filters as described in Examples 1-3. The lens used for the laser collimation and Raman focusing was a camera lens instead a simple achromatic doublet. A camera lens was used because it had much better imaging properties and fewer aberrations, in particular when it was used off axis as it is here. A diagram of the system is shown in FIG. 15. The system 1500 includes a sample lens 1510, first and second long pass filters (785 nm) 1520 and 1530, a 50 mm camera lens 1540, a 2×3 laser excitation array 1550 and a 2×3 Raman collection array 1560.

Using the camera lens largely improved the spot shape, giving round focused spots. The ferrules were on the right side of the lens—the same side the camera film detector would be (back of the lens), and the samples were on the front of the lens (where the subject would be). This arrangement was selected because the camera lens is optimized to work with diverging light at the back (the lens would normally focus light on the film/detector) and collimated light at the front (subject at infinity). Using the lens the wrong way can result in aberrations. A difficulty with using the same lens for both the laser and the Raman is that both arrays should be in the focal plane of the lens at the same time. Otherwise the array of focused laser spots may not have the same dimension as the array of focused Raman spots. Additionally, when the two arrays are not at the same distance from the camera lens, the focusing by the sample lens does not occur in the same plane, making the collection very inefficient.

Another difficulty is aligning the laser and Raman spots formed by the sample lens—any rotation of an array to align the focused spots (laser and Raman) formed by the sample lens is desirably not accompanied by a change in the distance between the rotated array and the camera lens. If the array moves with respect to the focal plane of the camera lens, then the focal plane of the sample lens for this array can move as well. This results in the focused Raman spots being aligned with the focused laser spot, but the focus does not occur in the same plane—and the collection is very inefficient. Experimentally, it is much easier to work with a sample lens that has a long focal length, so that the fiber arrays appear magnified in the focal plane of the sample lens. In this manner it is much easier to see the (mis)alignment of the Raman and laser spots, and rotate the arrays accordingly to achieve proper alignment. The sample lens can then be replaced by another lens with a shorter focal length (if desired), and the Raman and laser spots will still be aligned. Additionally, for the excitation and collection spots to be vertically aligned the height of each of the ferrules relative to the camera lens can be selected to be the same or substantially similar. If not, the angles of collimation of the Raman and laser are different, the focusing by the sample lens occurs at a different height, and the collection is inefficient.

Figure 16A:
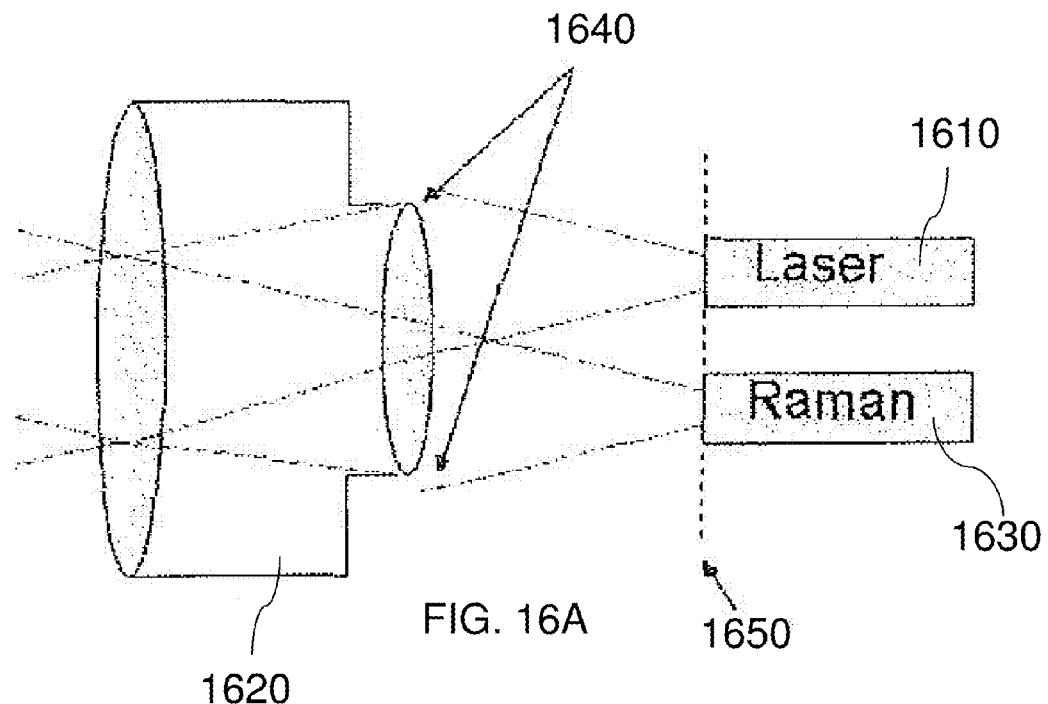
FIGS. 16A and 16B are representations showing vignetting (FIG. 16A) and no vignetting (FIG. 16B), in accordance with certain examples.
Figure 16B:
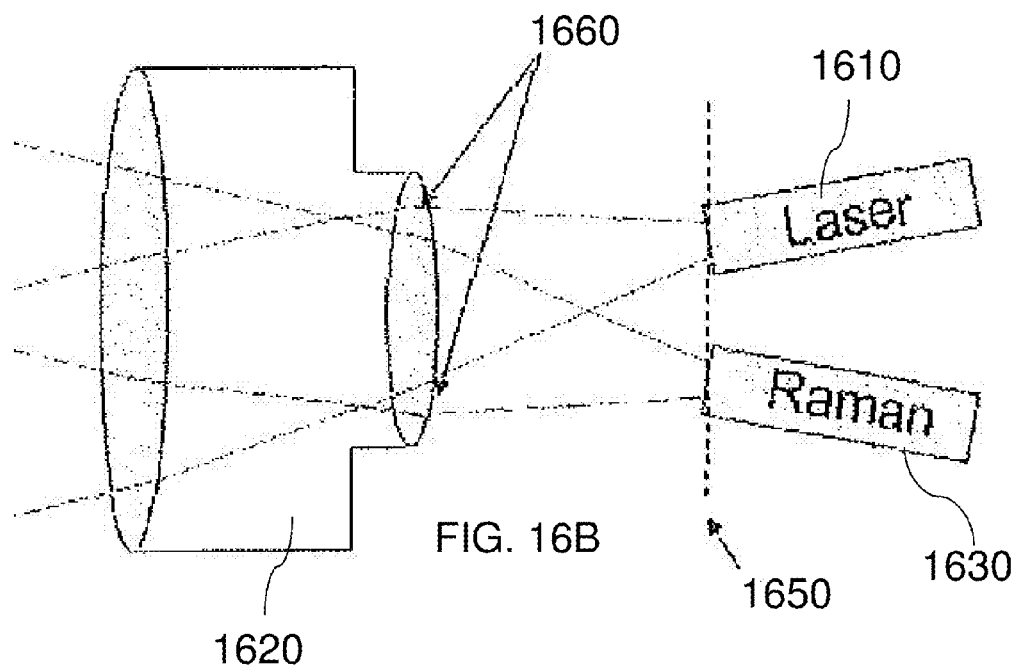

If the same lens is used for both the laser and the Raman, the excitation and collection fiber arrays may be off the axis of the camera lens. Referring to FIGS. 16A and 16B, in order to maximize the amount of light from laser fibers 1610 that reaches a camera lens 1620 and the amount of light from Raman scattering that are coupled with the collection fibers 1630, the ferrules can be rotated so that they face the camera lens 1620. Without the rotation, vignetting 1640 was observed (as shown in FIG. 16A), resulting in losses and strong scattering by the mount of the camera lens' back (made out of a metal, and quite reflective). By rotating the ferrules, the vignetting can be avoided or reduced (as shown by arrows 1660 in FIG. 16B), but the ferrules of the fibers may not be in the lens' focal plane 1650 any longer.

Figure 17:
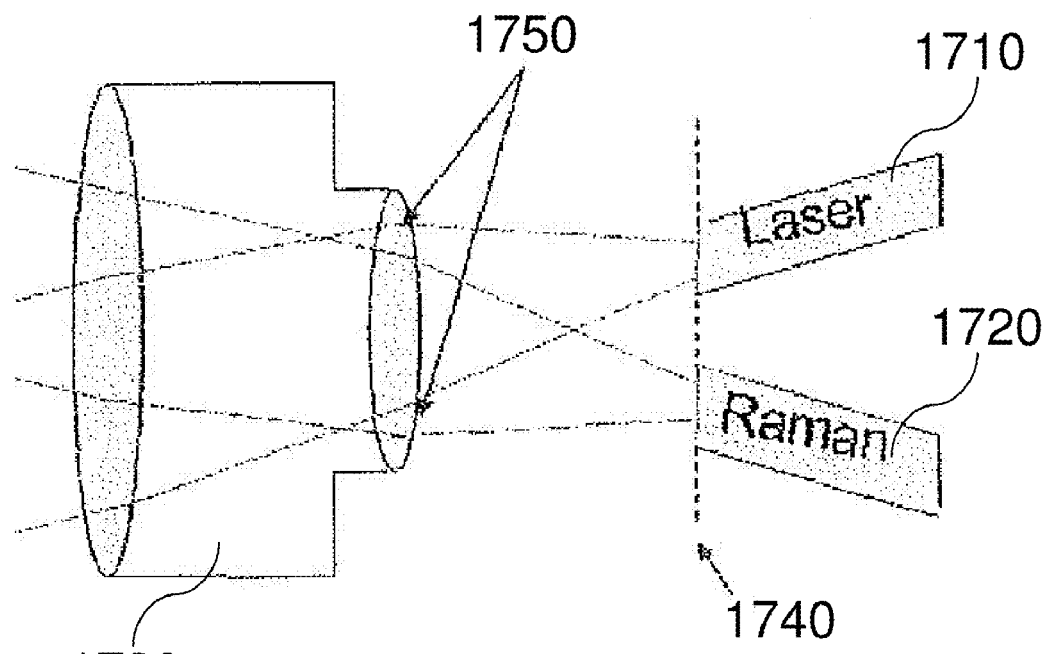
FIG. 17 is a representation showing beveled apertures for the excitation source and collection device, in accordance with certain examples.

With the rotation, the vignetting was completely avoided at the back of the camera lens. However, rotating the ferrules also resulted in the six fibers of each array not all being in the focal plane of the camera lens anymore. This had an effect on the efficiency of the coupling. This problem could be corrected by using a beveled instead of a cylindrical ferrule, and all the fibers could be maintained in the focal plane while facing the camera lens at the same time. Initially, the ferrules of the fibers were originally designed to be used separately with a dedicated lens, so rotation of the ferrules was not necessary for that application and the front of the custom made ferrules was therefore flat. Custom made ferrules with a different shape would avoid that issue, and still prevent vignetting as shown in FIG. 17. In particular the ferrules of the laser 1710 and the ferrules of the Raman collection fibers 1720 may be angled or beveled such that vignetting at the back of the lens 1730 is avoided (as shown by arrows 1750) while the fibers remain in the lens' focal plane 1740. More simply, using a lens with a larger f/# number would also achieve the same result.

With the long pass filters available used in the prototype, vignetting also occurred at the front of the lens because the filters (25 mm diameter, 22 mm clear aperture) were undersized (50 mm f/1.4 lens, with about 35 mm diameter at the front). This can be corrected by using larger filters (50 mm diameter) readily available from commercial suppliers. Because of the vignetting by the filter some losses occurred. The mounts holding the filters also scattered some of the laser.

During the collection of the Raman signal, some loss in the collection was also caused by the filters. Larger filters could avoid the occurrence of the issue. The overall efficiency of the system was reduced because: some of the laser was vignetted by the filters, reducing the excitation power; some of the emitted Raman was vignetted by the filter, reducing the collection efficiency; the fibers (excitation and collection) were not all in the focal plane of the lens because of the tilt of the ferrules, resulting in poor coupling of the collected Raman; and scattering by each of the surfaces of the multi element camera lens occurred (for both the laser and the Raman).

Because of the scattering by the camera lens' many surfaces, the tilt of the long pass filters used to combine the Raman with the laser and the scattering by the mounts of the various optical elements that vignetted the laser, the amount of laser entering the collection fibers was higher than desired. While it was not enough to generate any noticeable Raman by the silica of the collection fibers, it was enough to generate stray light on the detector. In order to avoid this result, extra laser filtration was used. This was achieved by placing a long pass filter directly in front of the Raman collection fiber (without obstructing the path of the laser), and placing another long pass filter inside the spectrometer itself.

The filter in front of the collection fibers was enough to reduce the laser line to some extent, but because the filter was not used with collimated light the filter's efficiency was not optimum. The size of this filter was enough to not cause any loss. The other filter was placed inside the spectrometer between the mirror and the grating, though it could also be placed between the mirror and the collimating lens. The use of the filter with collimated light resulted in a very large reduction of the stray laser to levels that did not cause any undesired results. However, because the filter had a 22 mm clear aperture and the rest of the optics' diameter was 50 mm, losses in the Raman signal occurred. A larger filter, e.g., 50 mm, would have filtered out the laser without reducing the Raman.

Figure 18:
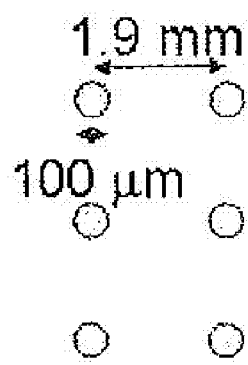
FIG. 18 shows spots produced for an excitation array, in accordance with certain examples.
Figure 19:
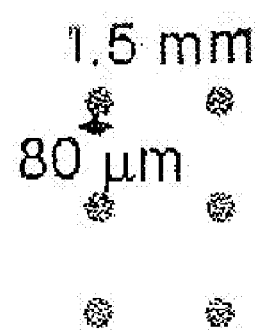
FIG. 19 shows spots produced for an image of the excitation array of FIG. 18, in accordance with certain examples.
Figure 20:
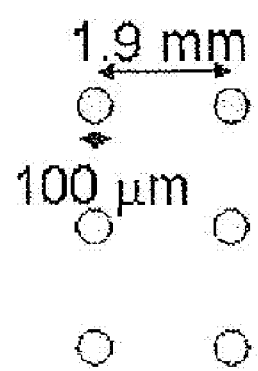
FIG. 20 shows spots produced for an image of the collection array, in accordance with certain examples.

Although the efficiency of the system was low for the reasons discussed above, it was sufficient enough to collect spectra to demonstrate proof of concept. The sample lens that was used during the collection (40 mm focal lens, 25 mm diameter) had a small diameter to limit the vignetting by the filters, and the focal length was chosen so that the f/# was high to achieve an efficient collection. This lens was chosen in order to not aggravate the efficiency issue. Because the focal length of the sample lens was less than the camera lens' focal length (50 mm), the focused laser spots were a demagnified image (ratio of 40/50) of the excitation array. As the fibers were 1.9 mm apart from each other in the array, the spots were about 1.5 mm apart. A single paracetamol tablet was used as the sample, and sampling was performed at six different locations simultaneously. The different spots produced for the excitation array, the image of the excitation array and the collection array are shown in FIGS. 18, 19 and 20, respectively.

Figure 22:
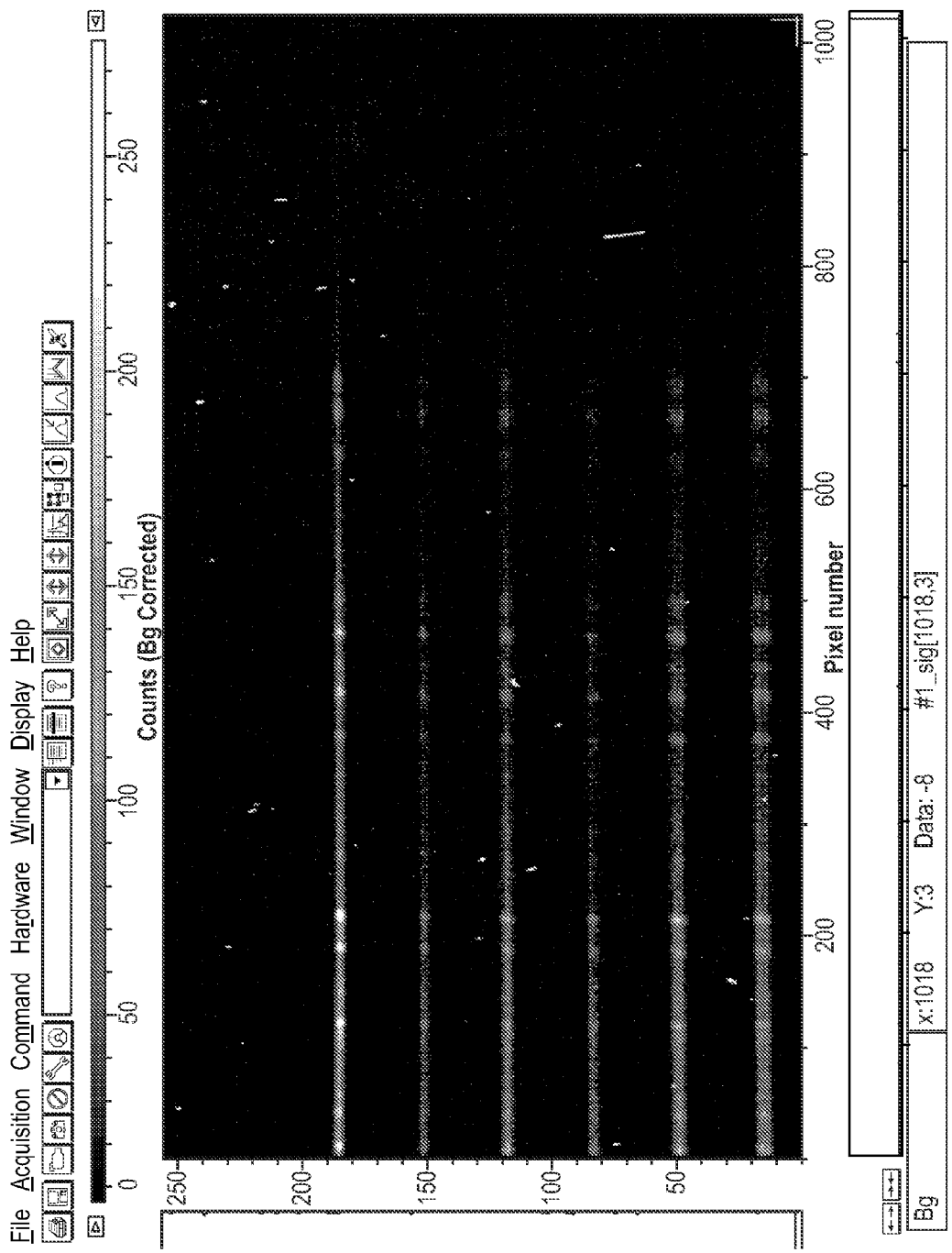
FIG. 22 is a detector image of paracetamol, in accordance with certain examples.

As shown in FIG. 22 (image of the detector), six tracks were visible. Each track corresponded to one of the collection fibers of the array. As the six fibers were collecting the spectrum of paracetamol, all the tracks have hotspots at the same position in the dispersion plane (horizontal). The intensity of the signal is not the same for all the tracks however because the laser power was not equal in the six excitation fibers, the coupling efficiency was not the same for the six collection fibers and vignetting affected the different fibers with a different severity.

EXAMPLE 7

Fluorescence Spectroscopy

The set of long pass filters used to fold the laser path and combine it with the Raman path can be modified to transmit a wider range of wavelengths (instead of the laser wavelength only), and collect the wavelengths longer than the excitation wavelength, e.g., fluorescence emissions or phosphorescence emissions. The amount of angle tuning necessary to transmit the excitation wavelengths can be determined using the above-listed equations.

With a range of excitation wavelengths, the filters can be used for fluorescence spectroscopy. Because fluorescence spectroscopy is less demanding than Raman spectroscopy (the intensity of the fluorescence compared to the excitation is much higher than the Raman intensity compared to the scattered laser), there is no need to use extra filters for filtration and two edge filters should be sufficient. The use of a single lens for the collection and the excitation, in particular, is more straightforward.

The small size of the optics remains the main advantage of the double edge design, since the excitation and the collection can come from the same direction. Using the multiplex properties of the system can be used to screen through large numbers of samples at the same time, or for imaging applications. In the latter case, the time necessary to complete the scanning of all the sampling points will be reduced by a factor equal to the number of simultaneous points.

When introducing elements of the examples disclosed herein, the articles "a," "an," and "the" are intended to mean that there are one or more of the elements. The terms "comprising," "including" and "having" are intended to be open ended and mean that there may be additional elements other than the listed elements. It will be recognized by the person of ordinary skill in the art, given the benefit of this disclosure, that various components of the examples can be interchanged or substituted with various components in other examples.

Although certain features, aspects, examples and embodiments have been described above, additions, substitutions, modifications, and alterations of the disclosed illustrative features, aspects, examples and embodiments will be readily recognized by the person of ordinary skill in the art, given the benefit of this disclosure.

What is claimed is:

1. An optical device comprising first and second optical elements, the first optical element angle-tuned to pass light received from an excitation source, and the second optical element optically coupled to the first optical element and angle-tuned to reflect incident light from the first optical element back to the first optical element and configured to pass light reflected from the first optical element, wherein the first and second optical elements are both long pass filters.

2. The optical device of claim 1, further comprising a collection device configured to receive sample light incident on the first and second optical elements and passed by the first and second optical elements to the collection device.

3. The optical device of claim 2, further comprising a detector optically coupled to the collection device.

4. The optical device of claim 1, in which the long pass filters are configured to pass scattered or emitted light from a sample to a detector optically coupled to the sample.

5. The optical device of claim 2, in which the collection device comprises an optical fiber bundle.

6. The optical device of claim 3, in which the detector is a charge-coupled device.

7. The optical device of claim 1, in which the optical device is configured to detect Raman scattered light.

8. A spectroscopic system, comprising:
   an excitation source configured to provide light, the excitation source comprising a plurality of optical fibers;
   a first optical element optically coupled to the excitation source and configured to pass light received from the excitation source, each optical fiber of the excitation source configured to provide light to the first optical element;
   a second optical element optically coupled to the first optical element, the first and second optical elements each angle-tuned such that the second optical element is configured to reflect incident light from the first optical element back to the first optical element and to pass light reflected from the first optical element;
   a sample space optically coupled to the second optical element and configured to receive the light passed by the second optical element; and
   a collection device optically coupled to the second optical element, in which the first and second optical elements are further configured to receive emitted light from a sample in the sample space and to provide the emitted light to the collection device.

9. The spectroscopic system of claim 8, in which the collection device comprises a plurality of optical fibers each configured to receive a light emission from a different sample in a multi-sample device in the sample space.

10. The spectroscopic system of claim 9, further comprising a detector optically coupled to the plurality of optical fibers each configured to receive the light emission.

11. The spectroscopic system of claim 8, in which the spectroscopic system is configured to detect Raman scattered light.

12. The spectroscopic system of claim 8, wherein the first and second optical elements are both long pass filters.

13. A system comprising:
   means for providing light to a sample space;
   a first optical path between the means for providing light and the sample space; and
   first and second optical means in the first optical path, the first optical means for passing light received from the means for providing light, and the second optical means optically coupled to the first optical means, the second optical means for reflecting incident light from the first optical means back to the first optical means and for passing the light reflected from the first optical means to the sample space.

14. The system of claim 13, further comprising means for detecting light emitted from the sample space, wherein said means for detecting light is optically coupled to the sample space through a second optical path and wherein the first optical means and the second optical means are in the second optical path and pass emitted or scattered light from the sample space to the means for detecting along the second optical path.

15. The system of claim 14, wherein said first optical means and said second optical means are each a long pass filter.

16. The system of claim 15, wherein said means for providing light comprises an optical fiber bundle optically coupled to a laser.

17. The system of claim 16, wherein said means for detecting light comprises an optical fiber bundle optically coupled to a charge-coupled device.

18. A method comprising:
   providing a sample space;
   providing an excitation source comprising a plurality of optical fibers configured to provide light to the sample space;
   selecting a first angle for a first optical element;
   selecting a second angle for a second optical element that is optically coupled to the first optical element;
   angle tuning the first and second optical elements by adjusting the selected first and second angles such that the first optical element is configured to pass light received from the excitation source, and the second optical element is configured to reflect incident light from the first optical element back to the first optical element and configured to pass the light reflected from the first optical element to the sample space;
   providing light to the first optical element with the plurality of optical fibers of the excitation source;
   reflecting incident light from the first optical element back to the first optical element:
   passing light reflected from the first optical element to the sample space; and
   detecting emitted light from the sample space with a detector.

19. The method of claim 18, wherein the first and second optical elements are both long pass filters.

20. A method of detecting emitted or scattered light comprising
   configuring a system with at least a first and second long pass filter;
   angle-tuning the first and second long pass filters such that the first long pass filter is configured to pass light received from an excitation source, and the second long pass filter is configured to reflect incident light from the first long pass filter back to the first long pass filter and configured to pass the light reflected from the first long pass filter to a sample; and
   detecting emitted light from the sample with a detector.

* * * * *